(12) United States Patent
Kamasaka et al.

(10) Patent No.: US 6,268,182 B1
(45) Date of Patent: *Jul. 31, 2001

(54) METHOD AND PRODUCING PHOSPHORYLATED SACCHARIDES

(75) Inventors: Hiroshi Kamasaka, Kawachinagano; Shigetaka Okada, Ikoma; Kaname Kusaka, Osaka; Kazuya Yamamoto, Amagasaki; Kenji Yoshikawa, Takatsuki, all of (JP)

(73) Assignee: Ezaki Glico Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/719,864

(22) Filed: Sep. 25, 1996

Related U.S. Application Data

(62) Division of application No. 08/514,478, filed on Aug. 11, 1995.

(30) Foreign Application Priority Data

Aug. 11, 1994 (JP) .................................... 6-222368
May 19, 1995 (JP) .................................... 7-121984

(51) Int. Cl.$^7$ .................................................. C12P 19/00
(52) U.S. Cl. .............................................. 435/72; 435/74
(58) Field of Search .................... 435/72, 74; 574/25; 536/1, 11

(56) References Cited

U.S. PATENT DOCUMENTS

| 3,494,916 | 2/1970 | Napier et al. ......................... 260/234 |
| 5,202,111 | * 4/1993 | Spalto et al. .............................. 424/49 |

FOREIGN PATENT DOCUMENTS

| 0512599 A2 | 11/1992 | (EP) . |
| 0514588 A2 | 11/1992 | (EP) . |
| 0675137 A2 | 10/1995 | (EP) . |
| 54-36388 | 3/1979 | (JP) . |
| 56-97248 | 8/1981 | (JP) . |
| 60-139703 | 7/1985 | (JP) . |
| 62-68793 | 3/1987 | (JP) . |
| 63-39597 | 2/1988 | (JP) . |
| 63-5008051 | 3/1988 | (JP) . |
| 2-215368 | 8/1990 | (JP) . |
| 3-240470 | 10/1991 | (JP) . |
| 05095765 | 4/1993 | (JP) . |
| 5-248939 | 11/1993 | (JP) . |
| 6-14790 | 1/1994 | (JP) . |
| 6-7116 | 1/1994 | (JP) . |
| 6-46797 | 2/1994 | (JP) . |
| 6-30599 | 4/1994 | (JP) . |

OTHER PUBLICATIONS

A.P. Croft. et al. (1983), "Synthesis of Chemically Modified Cyclodextrins," *Tetrahedron Report No. 147*, 39(9):1417, 1450, 1451, 1473, Lubbock, Texas.

S. Tabata, et al. (1978), "Action of Sweet–Potato Beta–Amylase on Phosphodextrin of Potato Starch," *Carbohydrate Research*, 67:189–195.

Aoki et al., "Whey Protein– and Egg White Protein–Glucose 6–Phosphate Conjugates with Calcium Phosphate–solubilizing Properties," *Biosci. Biotech. Biochem.* 58(9):1727–1728 (1994).

Goto, "Interactions of Calcium with Other Nutrients in Intestinal Absorption," *Jap. Soc. Nutr. Food Sci.* 32(1):1–11 (1979) (with partial translation).

Hamada et al., "Role of Oligosaccharides in Dental Caries Development," *J. Jpn. Soc. Starch Sci.* 2:83–91 (1984) (with partial translation).

Kato et al., "Excellent Emulsifying Properties of Protein–Dextran Conjugates," *American Chemical Society*, Chapter 16, pp. 213–229 (1991).

Kato et al., "Improvement of the Functional Properties of Insoluble Gluten by Pronase Digestion Followed by Dextran Conjugation," *J. Agric. Food Chem.* 39:1053–1056 (1991).

Miyake et al., "Effects of Sodium Polyphosphate on the Inhibition of Calculus Formation In vitro and Animal Test," *J. Japan Soc. Periodont.* 30(3):860–867 (1988).

Naito, "The Mechanism of Enhancement in Intestinal Calcium Absorption with Phosphopeptides Derived During Casein Digestion," *Jap. Soc. Nutr. Food Sci.* 39(6):433–439 (1986).

Sakanaka, "Anti–caries Effects of Tea Polyphenols," *Fragrance Journal* 11:42–49 (1990).

Takeda et al., "Location of Phosphate Groups in Potato Amylopectin," *Carbohydrate Research* 102:321–327 (1982).

Takeda et al., "Actions of Porcine Pancreatic and *Bacillus Subtilis* α–Amylases and *Aspergillus Niger* Glucoamylase on Phosphorylated (1→4)–α–D–Glucan," *Biochimica et Biophysica Acta* 749:302–311 (1983).

Tanaka et al., "The Physiological Mechanism of Watercore in Japanese Pear (*Pyrus Pyrifolia* Nakai Var. Culta Nakai) and its Prevention by Calcium EDTA," *J. Japan. Soc. Hort. Sci.* 61(1):183–190 (1992).

Yagi et al., "The Ash Content of Potato Starch in Hokkaido," *Denpun Kagaku* 20(2):51–58 (1973) (with partial translation).

Abe et al., (1982), "Action of Glucoamylase from *Aspergillus Niger* on Phosphorylated Substrate, " *Biochimica et Biophysica Acta* 703:26–33.

Takeda et al. (1982), "Location of Phosphate Groups in Potatoe Amylopectin, " *Carbohydrate Research* 102:321–327.

\* cited by examiner

*Primary Examiner*—Elli Peselev
(74) *Attorney, Agent, or Firm*—Dianne E. Reed; Reed & Associates

(57) ABSTRACT

Phosphorylated saccharide of the present invention includes at least one phosphate group in its molecule, selected from the group consisting of glucan, mannan, dextran, agar, cyclodextrin, fucoidan, gellan gum, Locust bean gum, guar gum, tamarind gum, and xanthan gum.

6 Claims, 16 Drawing Sheets

(1 of 16 Drawing Sheet(s) Filed in Color)

METHOD AND PRODUCING PHOSPHORYLATED SACCHARIDES

CROSS-REFERENCE TO RELATED APPLICATIONS

This application is a divisional of U.S. Ser. No. 08/514,478, filed Aug. 11, 1995.

BACKGROUND OF THE INVENTION

1. Field of the Invention

The present invention relates to saccharide which is phosphorylated (hereinafter, referred to as phosphorylated saccharide). More particularly, the present invention relates to a phosphorylated saccharide derivative which is a complex of phosphorylated saccharide and a protein or a peptide or to a phosphorylated saccharide derivative which is a conjugate of phosphorylated saccharide or a phosphorylated saccharide derivative and alkaline earth metal or iron.

The phosphorylated saccharide or phosphorylated derivative has the effect of inhibiting the precipitation (hereinafter, referred to as solubilization) of alkaline earth metal such as calcium or iron or has the effect of promoting the absorption of calcium. Accordingly, the present invention is useful as raw materials, compositions for foods and drinks, compositions to be added to foods, or raw materials or compositions for feeds which prevent various kinds of diseases by promoting the absorption of alkaline earth metal such as calcium or iron contained or allowed to be contained in foods, drinks, feeds, or fertilizers into a living body to improve health of a human or an animal.

The present invention also relates to a raw material and a composition for a fertilizer which promotes the absorption of calcium into plants or fruits to allow the plants or fruits to hold longer. Furthermore, the present invention also has the effect of preventing carious teeth. Specifically, the present invention can be added to oral compositions such as tooth paste, mouth wash, and troche, as well as foods, drinks, and feeds. The present invention can be used as a scale preventive capable of preventing or suppressing the generation of various scales, in particular, calcium scales and magnesium scales.

2. Description of the Related Art

Among nutrients to be taken from foods, minerals are indispensable for maintaining the function of bones, nerves, and muscle. However, in daily life, people are not likely to take sufficient minerals; therefore, the influence of insufficient absorption of the minerals on health has been raised as a problem.

For example, the average intake of calcium has not reached its required amount, which is set at a high level, such as 600 mg in Japan, because of low absorption ratio of calcium in a body. Thus, it is important to increase the absorption ratio of calcium in a body. The reasons why calcium is not likely to be absorbed in a body are as follows: calcium has been known to form an insoluble precipitation (i.e., calcium phosphate) by binding to inorganic phosphate in an alkaline region. The atmosphere in intestine is weak alkaline and recent processed foods contain a great amount of inorganic phosphate; therefore, calcium taken in a body becomes calcium phosphate to be precipitated. This prevents calcium from being absorbed through the intestine.

It is important to allow calcium to be efficiently absorbed through the intestine in the atmosphere thereof. In particular, growing infants and pregnant women need a large quantity of calcium. Furthermore, osteoporosis caused by insufficient digestion of calcium is also a serious problem. Osteoporosis is caused by a reduction in the ability of the intestine to absorb calcium which occurs with age. Examples of calcium-rich foods include dairy products such as milk, yogurt, and cheese; and dried products or food boiled down in soy of sea foods such as a sardine and a shrimp. In some cases, these foods are not likely to be taken in, because of preference and the decrease in masticatory power.

As for the ingestion of iron, divalent iron is likely to be oxidized to change to a trivalent iron. Oxidized iron coagulates in a neutral to alkaline region to form a precipitation, and hence becomes difficult to be absorbed by a living body. The absorption ratio of iron in a living body is greatly varied depending upon the food which contains the iron; thus, it cannot be said that the ingestion of iron by people of today who are likely to have an unbalanced diet is sufficient. Particularly, women are supposed to take in a considerable amount of iron; therefore, a low intake thereof causes a problem.

Magnesium phosphate, like calcium phosphate, is insoluble. The absorption ratio of magnesium in a living body is relatively low; therefore, insufficient digestion thereof, especially by growing infants and pregnant women, causes a problem. The absorption ratio of magnesium in a living body is also likely to vary depending upon the food which contains the magnesium.

Growing infants and pregnant women are unlikely to absorb sufficient amount of the above-mentioned minerals; therefore, they are required to take in much more of these minerals. Furthermore, recently, problems involving weight control and an unbalanced diet are getting serious. Thus, foods, especially luxury foods which allow iron and magnesium as well as calcium contained therein to be effectively absorbed by a living body are demanded, and it is important to develop an ingestion method for promoting the absorption of these minerals.

In the case where calcium, magnesium, iron, or the like is added to drinks for the above-mentioned purposes, precipitates are generated while they are kept, resulting in the loss of effective components. Furthermore, excess addition of calcium has been known to cause the decrease in utility of a protein (Goto et al., "J. Jap. Soc. Nutr. Food Sci." vol. 32, pp. 1–11, 1979) or the decrease in utility of minerals (Naito et al., "J. Jap. Soc. Nutr. Food Sci.", vol. 39, pp. 433–439, 1986).

In the livestock industry, the rapid growth of broilers, pigs, and the like has been demanded in an attempt to improve the productivity; however, their bones cannot catch up with such a rapid growth. As a result, the livestock end up having weak legs and being deformed. Calcium is added to foods or the like particularly for the purpose of strengthening bones, improving egg shells, reinforcing calcium in milk, and preventing the bending of eels' bones; however, a low utilization factor of calcium in animals causes a serious problem.

Calcium is also a very important element for plants. It has been known that the administration of chelate calcium such as EDTA-calcium strengthens cell walls or suppresses the generation of ethylene gas to retard aging and to improve the keeping quality (K. Tanaka et al., J. Japan. Soc. Hort. Sci., vol. 61, pp. 183–190, 1992). However, since EDTA-calcium has toxicity, the development of a chelating agent which is safe and effective has been desired.

A material capable of forming a compound together with calcium, which prevents calcium from being insolubilized in the atmosphere of the intestine to allow calcium to be efficiently absorbed through intestine, has been developed and utilized. For example, a technique of adding casein phosphopeptide (CPP) to drinks or foods (Japanese Laid-Open Patent Publication Nos. 3-240470 and 5-284939); a calcium solubilization effect of a complex of calcium citrate and calcium malate (Japanese Laid-Open Patent Publication No. 56-97248); and a bone strength enhancing effect of calcium pectate (Japanese Laid-Open Patent Publication No. 6-7116) have been known. These compounds have already been utilized partially for foods. However, the use of these compounds is limited depending upon the purpose; thus, they are not necessarily satisfactory.

For example, casein phosphopeptide has a great effect on the absorption of calcium, and therefore is comparatively often used for foods. This peptide constitutes lactoprotein contained in milk. However, the lactoprotein is contained in milk in a small amount and is not easy to fractionate; therefore, the lactoprotein is very expensive. Furthermore, products which are not sufficiently refined, in other words, those containing bitter peptides in addition to casein phosphopeptide are not preferable in terms of taste.

Acidic polysaccharide or acidic proteins have also been known to have the ability of forming a compound with calcium. These polysaccharide or proteins are macromolecules, which increase the viscosity when added to foods; therefore, their use is limited. Furthermore, organic acids such as malic acid and tartaric acid are cheap but exhibit unfavorable taste when added to foods. These organic acids also have a problem in terms of the health of teeth because they sometimes decalcify the enamelum of teeth.

Dentalis lapis and bacterial plaque have been known to cause gingivitis, periodontitis, or dental caries. Although the detail of the formation of dentalis lapis has not been clarified, the formation is considered as a calcification phenomenon that calcium or phosphorous supplied from saliva and exudate is deposited on organic substrates such as bacteria, which constitute plaque, and saliva glycoprotein, to be crystallized. As for existing dentalis lapis inhibitors, there are proposals by Miyake et al. (J. Japan. Soc. Periodent, vol. 30, No. 3, pp. 860–867) regarding sodium pyrophosphate or sodium tripolyphosphate. Caries are formed as follows: *Streptococcus mutans* (strain 6715) forms non-water-soluble glucan, using sucrose as a nutrient source, under action of enzyme, glycosyltransferase (hereinafter, abbreviated as GTase). Glucan which covers the surface of teeth causes bacterial plaque. When *Streptococcus mutans* is acid-fermented in the bacterial plaque, teeth start melting to form dental caries. As non-cariogenic saccharides, some oligosaccharides which do not become a nutrient source for *Streptococcus mutans* have been proposed. (S. Hamada et al., J. Jpn. Soc. Starch Sci., vol. 31, pp. 83–91, 1984). Furthermore, as cariostatic agents, polyphenol which is a component of tea has been reported and utilized (S. Sakanaka et al., Fragnance Journal, vol. 11, pp. 42–49, 1990). However, the use of polyphenol is limited, because it also involves a problem with taste. Accordingly, a material having an effect on both dentalis lapis and bacterial plaque has yet been developed.

In general, as properties of oligosaccharide, those related to low-calorie and function of preventing intestinal disorders have been reported in great number; however, those related to phosphorylated saccharide have not been reported.

Gelatinized starch has high viscosity. This is attributable to the fact that amylopectin in starch is a long chain molecule having a number of branches. In the case where maltose or cyclodextrin is produced using starch as a raw material, gelatinized starch is difficult to handle because of its high viscosity. For example, when gelatinized starch having a concentration at a certain level or more is transported through a pipe, the pipe will be clogged with the starch.

As described above, the characteristics (low solubility, retrogradation, and high viscosity) of existing starch limit the use thereof in foods and other fields. Under these circumstances, a study was conducted, for improving the solubility and retrogradation resistance of starch by subjecting starch to an enzyme treatment, a chemical treatment, or a physical treatment so that the starch degrades into smaller molecule; as a result, retrogradation of starch was suppressed to a certain degree. However, it is difficult to prevent an excess decrease in molecular weight and intrinsic characteristics of starch, which is originally a macromolecule, will be lost.

The generation of scales in various kinds of industrial water systems is a serious problem irrespective of whether it is a high-temperature water system or a non-high-temperature water system. For example, when a water system is heated, metal ions such as calcium and magnesium which are contained in the water system in a dissolved state are likely to change to insoluble compounds, and deposit as scales on the heat conducting surface which is in contact with the water system. This phenomenon noticeably occurs in high-temperature water systems such as a boiler, a desalting device, and a device for utilizing geothermal hot water, which causes the decrease in thermal efficiency, blocking of a water path, etc.

In most starches stored by plants, phosphate groups are partially bound by an ester linkage to glucose constituting starch. Although starch generally contains phosphate in a small amount, starch of potatoes, particularly white potato is likely to contain a relatively large amount of phosphoric acid (T. Yagi et al., Denpun Kagaku, vol. 20, p. 51, 1973). It has been known that a phosphate group is bound by an ester linkage to a glucose residue at the 3-position and 6-position thereof in potato starch (Y. Takeda et al., Carbohydrate Research, vol. 102, pp. 321–327, 1982). In the case where such starch is degraded with starch degrading enzymes such as amylase, the enzyme cannot act on the vicinity of a glucose residue where a phosphate group is bound by an ester linkage in potato starch. Thus, it has been known that phosphorylated saccharide remains without degradation at a time of the completion of saccharification. It has also been known that for this reason, phosphorylated saccharide is disposed of as a disposal without its composition being known in the starch saccharification industry for producing oligosaccharide, maltose, and glucose.

In the starch saccharification industry, the step of allowing a saccharide solution to pass through an ion exchange resin is used for the purpose of removing enzymes used for saccharification and remaining phosphorylated saccharide from the saccharified solution.

In the above step, phosphorylated saccharide adsorbed by the ion exchange resin is eluted therefrom when the ion exchange resin is washed with a sodium hydroxide solution for reproducing the resin. The solution containing phosphorylated saccharide after being washed has been disposed of as a liquid waste. Because of strong alkalinity, phosphorylated saccharide contained therein is decomposed to be phosphoric acid and neutral saccharide or a reduced end of the saccharide is oxidized; therefore, the phosphorylated saccharide in the liquid waste remains at a low rate.

On the other hand, starch (hereinafter, it may be referred to as chemically modified starch) to which a phosphate group is chemically bonded has been known. According to the standards of food additives in Japan, in the case where phosphorylated starch is used as a food additive, it is required that phosphorus bound to the starch be contained in an amount of 0.2 to 3%, and free inorganic phosphate which is not bound to the starch be contained in an amount of 20% or less, based on the total amount of phosphorus.

Studies regarding the formation of a compound or a complex of phosphorylated saccharide or chemically modified starch with alkaline earth metal such as calcium or iron; those regarding the promotion of the absorption of alkaline earth metal such as calcium and iron into a living body, using phosphorylated saccharide; and those regarding detergents and dentalis lapis inhibitors using phosphorylated saccharide have not been conducted.

SUMMARY OF THE INVENTION

The phosphorylated saccharide of the present invention includes at least one phosphate group in its molecule, selected from the group consisting of glucan, mannan, dextran, agar, cyclodextrin, fucoidan, gellan gum, Locust bean gum, guar gum, tamarind gum, and xanthan gum.

In one embodiment of the invention, the saccharide is glucan having at least one phosphate group per molecule.

In another embodiment of the invention, the saccharide is glucan composed of 3 to 5 glucoses which are $\alpha$-1,4 bound to each other, and one phosphate group is bound to the glucan.

In another embodiment of the invention, the saccharide is glucan composed of 2 to 8 glucoses which are $\alpha$-1,4 bound to each other, and two phosphate groups are bound to the glucan.

In another embodiment of the invention, the saccharide is glucan including $\alpha$-1,4 bound glucose as a main chain and $\alpha$-1,6 bound and/or $\alpha$-1,4 bound glucose as a side chain.

Alternatively, phosphorylated saccharide derivative obtained by binding the above-mentioned phosphorylated saccharide to a protein or a peptide is provided.

Alternatively, phosphorylated saccharide derivative by binding the above-mentioned phosphorylated saccharide or the above-mentioned phosphorylated saccharide derivative to alkaline earth metal or iron.

According to another aspect of the invention, a method for producing the above-mentioned phosphorylated saccharide is provided, which includes the step of degrading starch having a phosphate group or chemically modified starch.

Alternatively, a method for producing the above-mentioned phosphorylated saccharide is provided, which includes the step of allowing starch degrading enzyme, glycosyltransferase, $\alpha$-glucosidase, or a combination thereof (provided that only a $\alpha$-glucosidase is excluded) to act on starch having a phosphate group or chemically modified starch.

In one embodiment of the invention, the starch degrading enzyme is selected from the group consisting of $\alpha$-amylase, $\beta$-amylase, glucoamylase, isoamylase, pullulanase, neopullulanase, and a combination thereof.

In another embodiment of the invention, the glycosyltransferase is cyclodextrin glucanotransferase.

Alternatively, a method for producing phosphorylated saccharide is provided, which includes the step of allowing glycosyltransferase to act on the above-mentioned phosphorylated saccharide.

In one embodiment of the invention, the glycosyltransferase is cyclodextrin glucanotransferase.

In another embodiment of the invention, the above-mentioned method includes the step of allowing a salt of alkaline earth metal or an iron salt to act on phosphorylated saccharide.

According to another aspect of the invention, fertilizers, feeds, foods, drinks, oral compositions, detergent compositions, and additive compositions thereof are provided, which include the above-mentioned phosphorylated saccharide or the above-mentioned phosphorylated saccharide derivative.

Alternatively, fertilizers, feeds, foods, drinks, oral compositions, detergent compositions, and additive compositions thereof are provided, which include the above-mentioned phosphorylated saccharide or the above-mentioned phosphorylated saccharide derivative bound to the phosphorylated saccharide.

Alternatively, fertilizers, feeds, foods, drinks, oral compositions, detergent compositions, and additive compositions thereof are provided, which include phosphorylated saccharide or derivative thereof.

Thus, the invention described herein makes possible the advantages of (1) providing a phosphorylated saccharide capable of reacting with minerals such as calcium, magnesium, and iron to form a compound or a complex, thereby preventing the insolubilization of these minerals; and (2) providing fertilizers, feeds, foods, drinks, oral compositions, detergent compositions, or compositions to be added thereto, using phosphorylated saccharide.

These and other advantages of the present invention will become apparent to those skilled in the art upon reading and understanding the following detailed description with reference to the accompanying figures.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DESCRIPTION OF THE PREFERRED EMBODIMENTS

Figure 1:
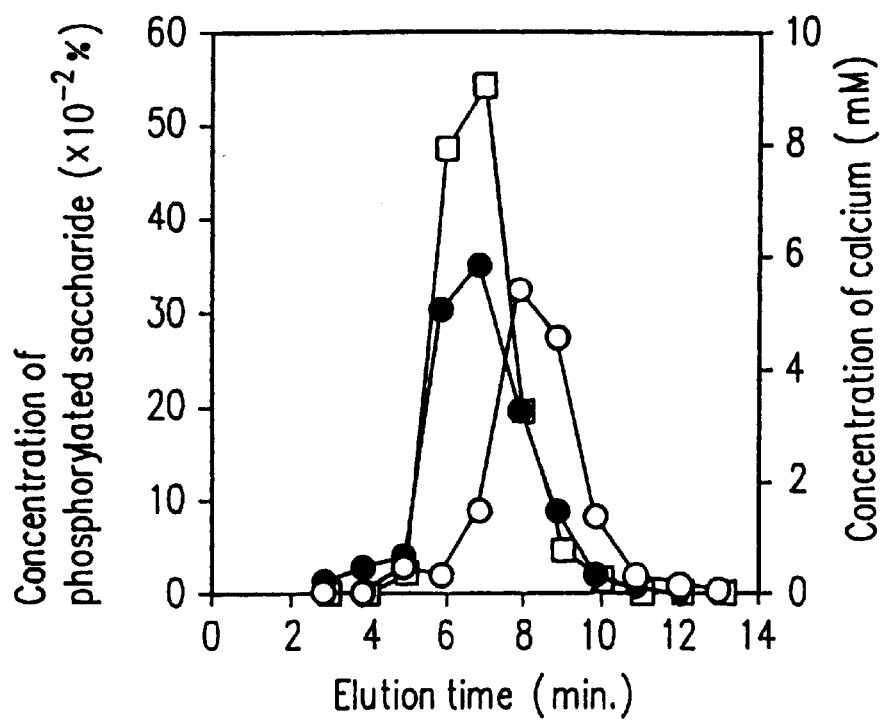
FIG. 1 is a graph showing a gel filtration elution pattern of a phosphorylated saccharide solution and a calcium chloride solution obtained in Example 1 of the present invention.

Hereinafter, the present invention will be described by way of illustrative examples with reference to the drawings.

The term "phosphorylated saccharide" as used herein refers to saccharide which is phosphorylated and has at least one phosphate group in its molecule. The term "neutral saccharide" as used herein refers to saccharide with no phosphate group linked thereto.

Examples of saccharides which can be used as raw material for producing phosphorylated saccharide of the present invention include glucan, mannan, dextran, agar, cyclodextrin, fucoidan, gellan gum, Locust bean gum, guar gum, tamarind gum, and xanthan gum. Hereinafter, the case of glucan will be described. General crude plant starch, preferably starch with a number of phosphate groups bound thereto, such as potato starch, purified starch, chemically modified starch, and various kinds of saccharides with phosphate groups chemically bound thereto are preferably used for producing the phosphorylated saccharide. In potato starch, a phosphate group is often bound by an ester linkage to the 3-position and 6-position of glucose as a constituent saccharide of the starch. A phosphate group is mainly present in amylopectin.

In order to enzymatically degrade starch or the like, at least one selected from the group consisting of starch degrading enzymes such as α-amylase (EC 3.2.1.1), β-amylase (EC 3.2.1.2), glucoamylase (EC 3.2.1.3), isoamylase (EC 3.2.1.68), pullulanase (EC 3.2.1.41), and neopullulanase (Kuriki et al., Journal of Bacteriology, vol. 170, pp. 1554–1559, 1988); and glycosyltransferase such as cyclodextrin glucanotransferase (EC 2.4.1.19; hereinafter, referred to as CGTase) is allowed to act on the starch. Alternatively, at least one of those enzymes and α-glucosidase (EC 3.2.1.20) are allowed to act on the starch.

Phosphorylated saccharide having no branch structure can be obtained by degrading starch with isoamylase or pullulanase to cleave α-1,6 branch structure from the starch. If these enzymes are not used, phosphorylated saccharide having α-1,6 branch structure can be obtained. By degrading phosphorylated saccharide with glucoamylase, non-phosphorylated glucose which is bound to a non-reduced end of phosphorylated saccharide can be sequentially liberated. Such an enzyme treatment enables the number of phosphate groups per molecule of purified phosphorylated saccharide to increase or decrease.

In other words, when phosphorylated saccharide high in phosphate content is required, starch is reacted with a large amount of the enzyme for a long period of time; when phosphorylated saccharide low in phosphoric acid content is required, starch is reacted with a small amount of the enzyme for a short period of time.

A number of different kinds of enzymes can be simultaneously reacted with a starch. Specifically, the starch as a raw material is first dissolved in water or a buffer with its pH adjusted so that the enzyme can act on starch. Then, liquefying α-amylase, pullulanase, glucoamylase, etc. are simultaneously added to a reaction solution, and the resulting solution is allowed to react by heating. According to this method, while starch is being gelatinized, neutral saccharide can be liberated, non-phosphorylated glucose which is bound to a non-reduced end of phosphorylated saccharide can be liberated, or α-1,6 branch structure derived from a material in phosphorylated saccharide structure can be cleaved. Accordingly, this method makes it possible to obtain phosphorylated saccharide with an increased content of phosphate by a one-step reaction, instead of a two-step reaction.

In the case where an enzyme reaction including two or more steps is conducted, i.e., a plurality of kinds of enzymes are acted on the starch in separate steps, the order of enzymes to be added to the starch is not specified. However, when starch is in high concentration, it is preferred that the starch is first acted on by enzyme including liquefying amylase. When isoamylase or pullulanase is allowed to act on the starch, the content of amylose in the resulting starch increases. Amylose is more likely to retrograde and precipitate compared with amylopectin, and thus, the starch retrogrades and precipitates. As a result, the starch cannot be subjected to the reaction by other enzymes.

There is no special limit to which starch degrading enzymes, glycosyltransferase, and α-glucosidase to be used are derived from. For example, as for α-amylase, starch degrading enzyme formulations derived from Bacillus and Aspergillus are preferably used. As the reaction conditions of enzyme, temperature and pH at which enzyme can act will suffice. For example, a temperature in the range of 25° C. to 70° C., and pH 4–8 are preferably used.

First, starch as a raw material is dissolved in water or a buffer with its pH adjusted so that the enzyme can act on the starch. Liquefying α-amylase is added to the resulting solution and allowed to react by heating, whereby the starch is liquefied while being gelatinized. Thereafter, the liquefied starch is kept at a temperature of 20° C. to 80° C. for an appropriate period of time. Any amount of the liquefying α-amylase can be used, as long as it is sufficient for liquefying the starch. The preferable amount is in the range of 20 to 50,000 U. The retention time at this point can be arbitrarily set, as long as the starch is liquefied to such a degree that it will not retrodegrade during the subsequent steps. Preferably, the retention time is 30 minutes.

After the completion of the liquefaction, the enzyme is generally not required to be inactivated; however, it can be inactivated by a conventional method, i.e., by being kept at 100° C. for 10 minutes. Furthermore, insoluble substances can be removed by separation, using a conventional method such as centrifugation or film filtration. Thereafter, phosphorylated saccharide can be fractionated. When phosphorylated saccharide with an increased content of phosphate is desired, the additional steps described below are conducted.

More specifically, after the material is liquefied, glucoamylase, isoamylase, pullulanase, and α-glucosidase are added to the liquefied starch simultaneously or in an appropriate order so as to saccharify the starch. The saccharified starch is allowed to react such as at a temperature of 40° C. to 60° C. for 30 minutes to 40 hours, whereby neutral saccharide and non-phosphorylated glucose which is bound to a non-reduced end of phosphorylated saccharide can be liberated from the material and α-1, 6 branch structure in the phosphorylated saccharide structure, derived from the material can be cleaved. Any combination and adding order of glucoamylase, isoamylase, and pullulanase can be used. The adding amount and retention time of the enzymes can be determined depending upon the content of phosphate required of the phosphorylated saccharide to be obtained. It is preferred that 50 to 700 U of glucoamylase, 2 to 100 U of isoamylase, 2 to 100 U of pullulanase, and 50 to 700 U of α-glucosidase can be added. Preferably, immobilized enzymes can be used.

After the completion of the reaction of each enzyme, the enzyme is not particularly required to be inactivated; however, it can be inactivated by a conventional method, i.e., by being kept at 100° C. for 10 minutes. Furthermore, insoluble substances can be removed by separation, using a conventional method such as centrifugation or membrane filtration.

In order to purify phosphorylated saccharide from a saccharide mixture containing phosphorylated saccharide, an anion exchange resin can be used, because phosphorylated saccharide is an ionic substance unlike neutral saccharide. There is no particular kind of resin which can be used. Examples of suitable resins are Chitopearl BCW 2500 type (produced by Fuji Spinning Co., Ltd.), Anberlite IRA type (produced by Japan Organo Co., Ltd.), DEAE-cellulose (produced by Tosoh Co.), DEAE-Sephadex and QAE-Sephadex (produced by Pharmacia Aktiebolag), and QAE-CELLULOSE (produced by Biorad). The resin is equilibrated by using a buffer with its pH appropriately adjusted. For example, about 10 to 50 mM of an acetate buffer (pH 4–5) is preferably used. The equilibrated resin is packed into a column and a saccharide mixture containing phosphorylated saccharide is applied thereto. Neutral saccharide is removed by washing, and then phosphorylated saccharide adsorbed to the column is eluted with an alkaline solution or a salt solution.

In the case where phosphorylated saccharide is eluted by increasing the ionic strength of an eluent, there is no particular limit to the kind of a salt to be used. For example, any one of sodium chloride, ammonium bicarbonate, potassium chloride, sodium sulfate, ammonium sulfate, and the like can be used.

In the case where phosphorylated saccharide is eluted by changing the pH of an eluent into alkaline, there is no particular limit to the kind of an alkaline reagent to be used. For example, ammonia, sodium carbonate, or sodium hydroxide can be used. However, under a strong alkaline condition, phosphate groups are liberated from saccharide or the reduced-end of the saccharide is oxidized. Thus, phosphorylated saccharide is eluted preferably at a pH in the range of weakly acid to weakly alkali, and more preferably at a pH of 3–8.

In the above case, by eluting phosphorylated saccharide by increasing the salt concentration or pH of the eluent gradually or in a stepwise manner, the component of the phosphorylated saccharide can be fractionated depending upon the number of phosphate groups bound to the phosphorylated saccharide per molecule.

In order to purify phosphorylated saccharide from a saccharide mixture containing phosphorylated saccharide, activated charcoal can also be used instead of an anionic exchange resin. There is no particular limit to the kind of activated charcoal to be used; however, particle-shaped activated charcoal capable of being packed into a column is preferably used. Activated charcoal is prepared using a buffer, an acid, an alkali, a salt solution, and distilled water so that the adsorption ability of neutral saccharide excluding glucose is exhibited. For example, degassed activated charcoal having a uniform particle size packed into the column and washed with distilled water is preferably used. Phosphorylated saccharide can be obtained as a passed fraction by applying a sample to the column and allowing neutral saccharide to be adsorbed into the column.

In order to purify phosphorylated saccharide from a saccharide mixture containing phosphorylated saccharide, another method can also be used, in which phosphorylated saccharide is precipitated by the addition of alcohol having 1 to 3 carbon atoms. In other words, alcohol is added to a sample solution to allow only phosphorylated saccharide to be precipitated. It is desired that 3 or more volumes of alcohol are added to saccharide having 10% or more concentration.

The phosphorylated saccharide of the present invention forms a phosphorylated saccharide derivative and is likely to precipitate in the presence of a metal salt, preferably a calcium salt or an iron salt in addition to alcohol. For this reason, in the presence of a metal salt, phosphorylated saccharide is recovered more easily using even a small amount of alcohol, as compared with the case of using alcohol alone. Preferably, the phosphorylated saccharide is collected under an alkaline condition. There is no particular limit to the kind of the salt to be used; for example, calcium chloride, magnesium chloride, or ferrous chloride can be used because of their satisfactory solubility. The collection of a precipitate generated by the addition of alcohol is conducted by a general method such as decantation, filtration, and centrifugation. A phosphorylated saccharide derivative which is a compound of phosphorylated saccharide with a metal salt is precipitated with alcohol as described above. If required, the collected precipitate is re-dissolved in water or an appropriate solution and alcohol can be added again to the resulting solution. This step can be repeated. This step enables impurities such as neutral saccharide and an excess salt to be removed. In order to remove impurities, such as a salt, an ultrafiltration membrane can also be used.

A phosphorylated saccharide derivative is obtained as a precipitate by adding a metal salt to the saccharide mixture in addition to alcohol. Phosphorylated saccharide can be produced by removing the metal salt from the precipitate. The removal of the metal salt (desalting) can be conducted by a conventional method. The desalting can be easily conducted by using, for example, table-top desalting microacilyzer G3 (manufactured by Asahi Chemical Industry Co., Ltd.).

The solution of phosphorylated saccharide, phosphorylated saccharide, or phosphorylated saccharide derivative thus obtained can be concentrated or powdered by using a conventionally used drying method such as convecting drying, fluidized-bed drying, and vacuum drying. By removing alcohol, if required, phosphorylated saccharide or a phosphorylated saccharide derivative which can be eaten or those which can be used for fertilizers or detergents can be obtained.

In the case where phosphorylated saccharide is produced using chemically modified starch, generally, those of monoester type are produced by a dry process, and those of diester type are produced by a wet process. The number of phosphate groups to be bound can be varied depending upon the conditions. In accordance with the Food Additive Standards in Japan, phosphorylated saccharide having about 3% by weight of bound phosphate groups is preferable for foods. However, this does not apply to the case where phosphorylated saccharide is used for feeds, fertilizers, or detergents. Compared with naturally occurring starch, chemically modified starch has more bound phosphate groups; thus, phosphorylated saccharide, obtained as an enzyme action product from such chemically modified starch, has a high degree of polymerization and has a high content of bound phosphate. Thus, by subjecting chemically modified starch to an enzyme treatment using amylase, as described above, phosphorylated saccharide having one bound phosphate group to a plurality of bound phosphate groups per molecule can be generated. Therefore, the compound forming ability of the phosphorylated saccharide produced from the chemically modified starch with respect to calcium, iron, and magnesium increases with the increase in the number of bound phosphate groups.

The structure of the phosphorylated saccharide thus obtained can be analyzed as follows:

First, phosphate groups are removed from the phosphorylated saccharide. For example, a phosphorylated saccharide solution is mixed with a buffer (pH 9.4) of 60 mM sodium carbonate containing 10 mM magnesium chloride, 0.3 mM zinc chloride, and 0.05% sodium azide. Then, alkaline phosphatase (EC. 3.1.3.1; derived from *E. coli*; produced by Sigma Chemical Company) is added to the mixture thus obtained. The resulting mixture is allowed to react at an appropriate temperature for an appropriate period of time (e.g., at 40° C. for 18 hours). Alkaline phosphatase is removed by using an ultrafiltration membrane to terminate the reaction, whereby a reaction solution (hereinafter, referred to as Reaction Solution A) containing saccharide from which phosphorylated groups are removed (hereinafter, referred to as dephosphorylated saccharide) is obtained.

Then, for example, β-amylase (derived from sweet potato; produced by Sigma Chemical Company) dissolved in 200 mM acetate buffer (pH 4.8) is added to Reaction Solution A. The mixture is allowed to react at an appropriate temperature for an appropriate period of time (e.g., at 37° C. for 2 hours) to provide a reaction solution (hereinafter, referred to as Reaction Solution B). Likewise, glucoamylase (derived from Rhizopus; produced by Toyobo Co., Ltd.) dissolved in 60 mM acetate buffer (pH 4.5) is added to Reaction Solution A. The mixture is allowed to react at an appropriate temperature for an appropriate period of time (e.g., at 35° C. for 18 hours) to provide a reaction solution (hereinafter, referred to as Reaction Solution C).

Reaction Solutions A to C are analyzed to confirm products therein. The products of these reaction solutions can be confirmed by analyzing these solutions by high-speed liquid chromatography using an anion exchange resin column, CarboPac PA-100 (ø4×250 mm, manufactured by Dionex Corp.) or thin layer chromatography using silica gel and comparing the analyzed results with those of standard malto oligosaccharides having various degrees of polymerization. The elution of dephosphorylated saccharide using high-speed liquid chromatography can be conducted by increasing the concentration of 1 M sodium acetate, using 100 mM sodium hydroxide as a basic solution. The detection of the dephosphorylated saccharide can be conducted by pulsed amperometric detector (produced by Dionex Corp.). The analysis of the dephosphorylated saccharide by thin layer chromatography can be conducted by multi-developing the dephosphorylated saccharide with the solvent system acetonitrile/water (80/20 v/v), detected the saccharide by heating at 130° C. for 3 minutes after spraying of 50% sulfuric acid in methanol.

When Reaction Solution A is analyzed, the chain length of the phosphorylated saccharide can be confirmed. If only maltose, or maltose and maltotriose (and a slight amount of glucose) is detected when analyzing Reaction Solution B, the dephosphorylated saccharide can be confirmed to be glucan in which glucose is α-1,4-bound. Furthermore, if only glucose is detected when analyzing Reaction Solution C, the dephosphorylated saccharide can be confirmed to be made of α-bound glucose.

The average chain length of saccharide (hereinafter, represented by DP, using glucose as one unit) can be obtained from the content of saccharide at various degrees of polymerization, constituting the dephosphorylated saccharide. The total content of saccharide in the entire phosphorylated saccharide can be determined by the phenol-sulfuric acid method. The number of bound phosphate groups can be determined by inorganic phosphate obtained by subjecting the dephosphorylated saccharide to wet incineration (Starch-related saccharide experimental method, Biochemistry experimental method 19, M. Nakamura et al., p. 31, 1986, JSSP Tokyo). The number of bound phosphate groups per molecule can be calculated by using the amount of inorganic phosphate determined after the wet incineration of the dephosphorylated saccharide and DP in accordance with the following formula:

$$\text{(Number of average bound phosphate groups per molecule)} = \frac{\text{(Amount of inorganic phosphate determined after wet incineration (mol))}}{\text{(Total amount of saccharide in entire phosphorylated saccharide (g))} / \text{(Average molecular weight of dephosphorylated saccharide calculated from } DP\text{)}}$$

For example, by allowing glucoamylase, isoamylase, or pullulanase to act on potato starch after α-amylase, phosphorylated saccharide having a degree of –polymerization of 2 to 8 in which glucose is α-1,4-bound can be obtained. The phosphorylated saccharide thus obtained can be divided into two groups by a purification method using the above-mentioned anion exchange resin: phosphorylated saccharide in which one phosphate group is bound to α-1,4-glucan per molecule and two or more phosphate groups are bound to α-1,4-glucan per molecule.

If a phosphate group is bound to the 6-position of glucose in the phosphorylated saccharide obtained by allowing glucoamylase to act on potato starch as described above, the starch can be cleaved from a non-reduced end to right before the glucose with its 6-position bound by a phosphate group. Thus, the phosphorylated saccharide is oligosaccharide having glucose with its 6-position bound by a phosphate group at a non-reduced end or has a structure in which the second glucose from the non-reduced end has its 6-position bound by a phosphate group. If a phosphate group is bound to the 3-position of glucose in the phosphorylated saccharide, the second glucose from the non-reduced end has its 3-position bound by a phosphate group. This is apparent from the characteristics of glucoamylase of Hizukuri et al. (Biochmica et Biophysica Acta, vol. 749, pp. 302–311, 1983).

When CGTase is allowed to act on phosphorylated saccharide in which one phosphate group is bound to α-1,4-glucan per molecule, phosphorylated saccharide having a higher calcium solubilization effect can be obtained.

These phosphorylated saccharides have never been produced. The present invention has made it possible to fractionate these phosphorylated saccharides, by which the structures thereof were made clear. Furthermore, the existence of the phosphorylated saccharide in which two or more phosphate groups are bound to α-1,4-glucan has not been known.

The analysis of the phosphorylated saccharides thus fractionated makes it clear that a liquid waste which has been disposed of when various kinds of saccharide solutions are produced from potato starch also contains phosphorylated saccharide. In the starch saccharification industry, such phosphorylated saccharide is adsorbed by an anion exchange resin; however, the phosphorylated saccharide is not an intended product, so that it is eluted with a strong alkaline solution when the anion exchange resin is reproduced and is degraded.

The phosphorylated saccharides prepared as described above have the following characteristics.

(1) The phosphate groups bound to saccharide can prevent the precipitation of metals because of their high affinity with alkaline earth metal such as calcium and iron.

(2) The phosphorylated saccharides have an effect of promoting the absorption of alkaline earth metal such as calcium and iron into a living body.

(3) The phosphorylated saccharides are non-dental cariogenic saccharides, which do not become the nutrient source for *Streptococcus mutans* causing dental caries and do not generate glucan.

(4) The phosphorylated saccharides have a pH buffering ability, and the pH buffering ability is increased by the synergism in the presence of calcium carbonate.

(5) The phosphorylated saccharides are difficult to be digested by in-vivo enzymes and are hard to digest, being low in calories.

(6) The phosphorylated saccharides have an effect of preventing the retrogradation of starch.

(7) The phosphorylated saccharides have no flavor and taste.

These effects are not limited to phosphorylated saccharide obtained from potato starch. For example, these effects can be obtained from phosphorylated mannan derived from yeast. Phosphorylated saccharide obtained from dextran, agar, cyclodextrin, fucoidan, gellan gum, Locust bean gum, guar gum, tamarind gum, or xanthan gum have the same effects. Furthermore, phosphorylated saccharide can provide the above-mentioned characteristics, irrespective of the kind of saccharide. It is noted that saccharide chemically bound by a phosphate group is subject to the use limit under the Food Additive Standards in Japan as described above; however, this does not apply to the uses other than in foods.

The phosphorylated saccharide of the present invention is capable of forming a complex with protein or peptide. A derivative of phosphorylated saccharide can be made from the phosphorylated saccharide. The production of complexes utilizing a Maillard reaction between saccharide and protein has been conventionally conducted. The Maillard reaction is the one that will be effected even during cooking; thus, a reaction product is biologically safe. This reaction is effected by dehydrated condensation of the reduced end of saccharide with the amino group of protein. In the case of polysaccharide, 1 to 2 saccharide molecules is bound to one molecule of a protein, and in the case of monosaccharide, saccharide is bound to most of the amino groups of a protein (A. Kato et al., American Chemical Society., Ch. 16, pp. 213–229, 1991). As the functions of the complexes, the improvement of thermal stability and pH stability of a protein, the provision of emulsifying characteristics, the solubilization of water-insoluble proteins have been reported (A. Kato et al., J. Agric. Food Chem., vol. 39, pp. 1053–1056, 1991). Recently, it has been found that the calcium solubilization effect is obtained by allowing glucose-6-phosphate to be bound to a protein (T. Aoki et al., Biosci. Biotech. Biochem., vol. 58, No. 9, pp. 1727–1728, 1994). However, monosaccharide has high reactivity with respect to a protein and causes the protein to be denatured; thus, its effect and stability are not satisfactory. Furthermore, there have been no reports regarding derivatives obtained from the phosphorylated saccharide of the present invention and a protein.

In the case of using a derivative obtained from the phosphorylated saccharide of the present invention and a protein, the protein is less denatured, compared with the case where glucose-6-phosphate is used. Therefore, the resulting derivative can stably solubilize calcium for a relatively long period of time. The reason for this is considered to be that the reaction of oligosaccharide proceeds more gently and damages the protein less as compared with the reaction of monosaccharide. Accordingly, this is an excellent method for allowing an organic ligand to be easily bound to a protein. There is no particular limit to a protein to be used; however, proteins that are available at lower cost and safe as foods are preferred. Examples of such proteins include ovalbumin, casein, wheat protein, and soybean protein. Peptides obtained by hydrolyzing these proteins can also be used.

The phosphorylated saccharide of the present invention is capable of promoting the absorption of calcium into a living body in ingestion of fertilizers, feeds, or foods containing the phosphorylated saccharide. The phosphorylated saccharide forms a compound or a complex with alkaline earth metal such as calcium or iron, promoting the absorption of alkaline earth metal or iron into a living body. Examples of the metal include magnesium, and zinc, in addition to calcium. Thus, it can be expected that the present invention prevents the diseases caused by the shortage of calcium, such as osteoporosis. Furthermore, in recent years, problems involving weight control and an unbalanced diet are getting serious. Thus, foods, especially luxury foods which allow iron and magnesium as well as calcium contained therein to be effectively absorbed into a living body are demanded, and it is important to develop an ingestion method for promoting the absorption of these minerals. The phosphorylated saccharide or phosphorylated saccharide derivative of the present invention is safe and hard to digest, and is low in caloric content. As reported regarding oligosaccharide, this phosphorylated saccharide can be expected to have an effect of proliferating *Bifidobacterium bifidum* and a function of preventing intestinal disorders.

Furthermore, according to the present invention, the effect of solubilizing metal is exhibited in a safe region with respect to a living body; therefore, the phosphorylated saccharide of the present invention can be used for safe detergents effective on stains caused by the deposition of metal or used for preventives for dentalis lapis caused by the deposition of calcium on teeth. The characteristic of the phosphorylated saccharide of the present invention of preventing the calcification, in which calcium and phosphorus are deposited to be crystallized, prevents the generation of dentalis lapis. The phosphorylated saccharide of the present invention does not become a nutrient source for *Streptococcus mutans* which causes dental caries and does not generate non-water-soluble glucan. Thus, the phosphorylated saccharide of the present invention does not allow bacterial plaque to be generated; therefore, acid fermentation of *Streptococcus mutans* is not caused. Furthermore, the phosphorylated saccharide of the present invention has a buffering function and an effect of preventing pH from decreasing. Thus, the phosphorylated saccharide of the present invention has an effect of preventing the decrease in pH caused by lactic acid, a fermented product in bacterial plaque in foods or oral compositions without affecting flavor thereof. The phosphorylated saccharide can be added to oral compositions such as tooth paste, mouth wash, and troche. In addition, according to the present invention, the phosphorylated saccharide forms a complex with alkaline earth metal such as calcium or iron to promote the absorption of these metals into a living body. Likewise, the present invention makes it possible to promote the absorption of a slight amount of metal such as calcium into plants in alkaline soil and alkaline conditions. For example, according to the present invention, safe calcium absorption accelerating agents effective for improving the prevention of aging of cut flowers, orchards, and fruits and keeping quality thereof can be provided. The characteristic of the phosphorylated saccharide of forming a complex with metal is effective for scale preventives and detergents.

As is understood from the above, the phosphorylated saccharide of the present invention or derivatives thereof can be preferably used for the following purposes.

The phosphorylated saccharide of the present invention can be used for almost all compositions for eating or drinking or compositions for food additives. The compositions for eating or drinking are used for referring to a general term of human foods, feeds for animals or fish breeding, and pet foods. Specifically, the phosphorylated saccharide can be effectively used for liquid and powdery drinks such as coffee, tea, green tea, oolong tea, juice, processed milk, and sports drinks; baked goods such as bread, cookies, crackers, biscuits, cake, pizza, and pie; pastas such as spaghetti and macaroni; noodles such as wheat noodles, buckwheat noodles, and Chinese noodles; sweets such as a caramel, chewing gum, and chocolate; snacks such as rice crackers, and potato chips; frozen confectionery such as ice cream and sherbet; dairy products such as cream, cheese, powdery milk, condensed milk, and lactic drinks; Western confectionery such as jelly, pudding, mousse, and yogurt; Japanese confectionery such as a sweet bun, uirou (square-cut rice cake obtained by adding saccharide to the powder, followed by steaming), rice cake, and ohagi (rice ball covered with bean jam, soy-bean flour, or black sesame); seasonings such as soy sauce, sauce for dipping, soup for noodles, Worcestershire sauce, broth stock, stew stock, soup stock, mixed seasonings, curry powder, mayonnaise, and ketchup; canned or retort foods such as curry, stew, soup, and rice dishes; frozen foods such as ham, hamburger, meat balls, croquette, Chinese-style dumpling, fried rice, and rice ball; marine processed products such as refrigerated foods, fish paste cake, fish paste molded around a stainless steel rod; and rice products such as rice for a picnic lunch and sushi. Furthermore, the phosphorylated saccharide of the present invention can be used for milk for infants, weaning foods, baby foods, pet foods, feeds for animals, sports foods, nutrition auxiliary foods, and health foods, because of its ability of allowing calcium to be readily absorbed.

The phosphorylated saccharide of the present invention prevents calcium from precipitating and allows calcium to be readily absorbed into plants. Therefore, it can be used for liquid or powdery fertilizers and agents for improving of keeping quality for plants such as fruits and cut flowers.

The phosphorylated saccharide of the present invention can be used for scale preventives capable of preventing or suppressing the generation of various scales, particularly those of calcium type and magnesium type, in high-temperature water systems and non-high-temperature water systems. If required, the phosphorylated saccharide can be used together with other known agents.

The phosphorylated saccharide of the present invention can be used for tooth paste, mouth wash, troche, and a gargle.

The phosphorylated saccharide of the present invention can also be used for agents such as medicine for internal use and a bathing agent containing calcium, iron, magnesium, or the like.

According to the present invention, phosphorylated saccharide whose physiological function had not been known was produced and its structure and function were made clear. The physiological function refers to an effect that phosphorylated saccharide conveys minerals (e.g., alkaline earth metals such as calcium and magnesium, and iron) required for a living body to the intestine without insolubilizing them, and promoting the absorption of these minerals into the living body. As a result of the analysis of the structure of the phosphorylated saccharide, it was found that phosphorylated saccharide present in a liquid waste caused when glucose is industrially produced from potato starch had the same structure as that of the phosphorylated saccharide having the above-mentioned characteristics. Thus, according to the present invention, a new function of an industrial waste was found, and it was made possible to recycle the phosphorylated saccharide contained in the waste as a material, considering the effective use of resources.

EXAMPLES

The structure of the phosphorylated saccharide of the present invention was analyzed as follows:

First, phosphate groups were removed from phosphorylated saccharide. A buffer (pH 9.4) of 60 mM sodium carbonate containing 100 $\mu$l of 10 mM magnesium chloride, 0.3 mM zinc chloride, and 0.05% sodium azide was mixed with 100 $\mu$l of 3% solution of phosphorylated saccharide. To this mixture was added 100 $\mu$l of 30 U/ml of alkaline phosphatase (EC. 3.1.3.1.; derived from *E. coli;* produced by Sigma Chemical Company), and the resulting mixture was allowed to react at 40° C. for 18 hours. Alkaline phosphatase was removed by using an ultrafiltration membrane to terminate the reaction. Thus, a reaction solution (hereinafter, referred to as Reaction Solution A) containing saccharide (hereinafter, referred to as dephosphorylated saccharide) from which phosphate groups were removed was obtained.

Next, 5,000 U/ml of β-amylase (derived from sweet potato; produced by Sigma Chemical Company) dissolved in 10 $\mu$l of 200 mM acetate buffer (pH 4.8) was added to 10 $\mu$l of Reaction Solution A and kept at 37° C. for 2 hours (hereinafter, the solution thus obtained is referred to as Reaction Solution B). Likewise, 300 U/ml of glucoamylase (derived from Rhizopus; produced by Toyobo Co., Ltd.) dissolved in 10 $\mu$l of 60 mM acetate buffer (pH 4.5) is added to 10 $\mu$l of Reaction Solution A (hereinafter, the solution thus obtained is referred to as Reaction Solution C).

Reaction Solutions A to C were analyzed to confirm the products therein. The products of these reaction solutions were confirmed by analyzing these solutions by high-speed liquid chromatography using an anion exchange resin column, CarboPac PA-100 (ø4×250 mm, manufactured by Dionex Corp.) or thin layer chromatography using silica gel and comparing the analyzed results with those of standard malto oligosaccharides having various degrees of polymerization. The elution of dephosphorylated saccharide using high-speed liquid chromatography was conducted by increasing the concentration of 1 M sodium acetate, using 100 mM sodium hydroxide as a basic solution. The detection of the dephosphorylated saccharide was conducted by pulsed amperometric detector (produced by Dionex Corp.). The analysis of the dephosphorylated saccharide by thin layer chromatography was conducted by multi-developing the dephosphorylated saccharide with acetonitrile/water (80/20 v/v), detected the saccharide by heating at 130° C. for 3 minutes after spraying of 50% sulfuric acid in methanol.

By analyzing Reaction Solution A, the chain length of the phosphorylated saccharide was confirmed. Only maltose or maltose and maltotriose (and a slight amount of glucose) was detected when analyzing Reaction Solution B. Thus, the dephosphorylated saccharide was confirmed to be glucan in which glucose is α-1,4-bound. Furthermore, only glucose was detected when analyzing Reaction Solution C. Thus, the dephosphorylated saccharide was confirmed to be made of α-bound glucose.

The average chain length of saccharide (hereinafter, represented by DP, using glucose as one unit) was obtained from the content of saccharide at various degrees of polymerization, constituting the dephosphorylated saccharide. The total content of saccharide in the entire phosphorylated saccharide was determined by the phenol-sulfuric acid method. The number of bound phosphate groups was determined in inorganic phosphate obtained by subjecting the dephosphorylated saccharide to wet incineration (Starch-related saccharide experimental method, Biochemistry Experimental Method 19, M. Nakamura et al., p. 31, 1986, JSSP Tokyo). The number of bound phosphate groups per molecule was calculated by using the amount of inorganic phosphate determined after the wet incineration of the dephosphorylated saccharide and DP in accordance with the following formula:

$$\text{(Number of average bound phosphate groups per molecule)} = \frac{\text{(Amount of inorganic phosphate determined after wet incineration (mol))}}{\text{(Total amount of saccharide in entire phosphorylated saccharide (g))} / \text{(Average molecular weight of dephosphorylated saccharide calculated from } DP\text{)}}$$

Example 1

First, 1% solution of potato starch was rapidly heated to 100° C. while being dissolved in 5 ml of a solution containing 6 mM sodium chloride and 2 mM calcium chloride so as to be gelatinized. Then, 35 U of α-amylase (produced by Ueda Chemicals Co., Ltd.) was allowed to act on the gelatinized mixture and kept at 50° C. for 30 minutes. A small amount of the reaction solution thus obtained was taken to give 0.2% saccharide solution. Then, 1/10 volume of 0.01 M iodine-potassium iodide solution was added to the saccharide solution. The resulting mixture was confirmed to be negative in iodometry; thereafter, 2 U of pullulanase (produced by Hayashibara Biochemical Lab.) and 6 U of glucoamylase (produced by Toyobo Co., Ltd.) were allowed to act on the mixture at 40° C. for 20 hours simultaneously. The reaction was terminated, and the reaction solution was centrifuged. The supernatant was applied to an anion exchange resin column (Chitopearl BCW 2501; produced by Fuji Spinning Co., Ltd.) equilibrated with 20 mM acetate buffer (pH 4.5). The supernatant was thoroughly washed with the acetate buffer to remove neutral saccharide, followed by being eluted with the acetate buffer containing 0.5 M sodium chloride. Each eluted fraction was concentrated with an evaporator, desalted, and lyophilized to provide phosphorylated saccharide.

Example 2

The phosphorylated saccharide obtained in Example 1 was again applied to the anion exchange resin column (Chitopearl BCW 2501; produced by Fuji Spinning Co., Ltd.) equilibrated with 20 mM acetate buffer (pH 4.5). The column was thoroughly washed with the acetate buffer to remove neutral saccharide. Then, fractions were eluted with the acetate buffer containing 0.15 M sodium chloride and then with the acetate buffer containing 0.5 M sodium chloride. These fractions were desalted and lyophilized. The analysis of these fractions in accordance with the above-mentioned method for determining the structure indicated that phosphorylated saccharide (PO-1 fraction) in which one phosphate group was bound to α-1,4-glucan having 3 to 5 glucoses was obtained from 0.15 M sodium chloride-eluted fractions, and phosphorylated saccharide (PO-2 fraction) in which two or more phosphate groups were bound to α-1,4-glucan having 2 to 8 glucoses were obtained from 0.5 M sodium chloride-eluted fractions.

It can be determined whether or not the phosphorylated group of the phosphorylated saccharide is bound to glucose at 6-position by the method of Hizukuri et al. (Staerke, vol. 22, pp. 338–343, 1970). In other words, the amount of glucose-6-phosphate generated after the hydrolysis of the phosphorylated saccharide was determined using enzyme. Glucose-6-phosphate was stable with respect to acid, so that the generated amount thereof was determined with glucose-6-phosphate dehydrogenase. The PO-1 fraction and PO-2 fraction were analyzed by this method. As a result, it was determined that in the PO-1 fraction, about 75% phosphate groups were bound to the 6-position and the rest were bound to the 3-position or the 2-position. In the PO-2 fraction, it was determined that the phosphate groups were hardly bound to the 6-position.

Example 3

First, 1% solution of potato starch was rapidly heated to 100° C. while being dissolved in 5 ml of a solution containing 6 mM sodium chloride and 2 mM calcium chloride so as to be gelatinized. Then, 35 U of α-amylase (produced by Ueda Chemicals) was allowed to act on the gelatinized mixture and kept at 50° C. for 30 minutes. The resultant mixture was kept in a boiling water bath for 5 minutes to terminate the reaction. The solution thus obtained was centrifuged, and the supernatant was applied to an anion exchange column to collect fractions in the same way as in Example 1. These fractions were desalted and lyophilized to provide phosphorylated saccharide.

Example 4

First, 500 ml of 10% chemically modified starch (containing 4% bound phosphate; produced by Nippon starch chemical Corp.) was applied to an ultrafiltration membrane with a molecular weight of 10,000 (produced by Millipore; using Minitan Ultra Filtration System) and desalted. Thereafter, 2,500 U of α-amylase and 100 U of glucoamylase (produced by Amano pharmaceutical Co., Ltd.) were added to the starch and allowed to react at 50° C. for 180 minutes. The mixture was kept in a boiling water bath for 5 minutes to terminate the reaction. The reaction solution was immediately cooled down, and three-fold volume of ethanol was added thereto, whereby precipitate thus generated was collected by centrifuging. Then, 100 g of activated carbon was added to the precipitate thus collected to remove neutral saccharide by absorption. The resulting precipitate was subjected to membrane filtration and lyophilized to provide phosphorylated saccharide.

Example 5

First, 5 g of chemically modified starch (containing 4% bound phosphate) was dissolved in 100 ml of 1 N hydrochloric acid solution and heated at 100° C. for 15 minutes. The resulting solution was immediately cooled down and pH-adjusted to neutral with 1 N sodium hydroxide solution, followed by being desalted. Then, 50 g of activated carbon was added to the desalted solution to remove neutral saccharide by adsorption. The resulting solution was subjected to membrane filtration and lyophilized to provide phosphorylated saccharide.

Example 6

The ability of forming a compound of the phosphorylated saccharide with calcium, iron, or magnesium was confirmed by a gel filtration method. First, 100 μl of 100 mM calcium chloride solution was added to 100 μl of 10% solution of the phosphorylated saccharide in Example 1. The mixture was subjected to gel filtration analysis using a column (Sephadex G-10; manufactured by Pharmacia Aktiebolag, ø1.2×10 cm column) equilibrated with 20 mM Tris-HCl buffer (pH 7.4). As a result, the peak of the phosphorylated saccharide was identical with that of calcium, and they were simultaneously eluted. Thus, a compound of phosphorylated saccharide with calcium was taken. Also, 100 μl of 100 mM calcium chloride solution was applied to the column. FIG. 1 shows elution patterns of these solutions. Ferrous chloride and magnesium chloride were also applied to the column, whereby the influence by the phosphorylated saccharide was examined. These results are shown in FIGS. 2 and 3.

FIG. 1 shows gel filtration elution patterns of the following three kinds of solutions: 100 μl of solution of 10% phosphorylated saccharide in Example 1 (an eluate was measured by the concentration of the phosphorylated saccharide; represented by □ in the figure); 100 μl of solution of 100 mM calcium chloride when being subjected to filtration together with 100 μl of 10% phosphorylated saccharide in Example 1 (an eluate was measured by the concentration of calcium; represented by ● in the figure); and 100 μl of solution of 100 mM calcium chloride (an eluate was measured by the concentration of calcium; represented by ○ in the figure). In FIG. 1, the horizontal axis represents an elution time (minutes), the left and right vertical axes represent the concentration of the phosphorylated saccharide ($\times 10^{-2}$%) and that of calcium (mM), respectively.

Figure 2:
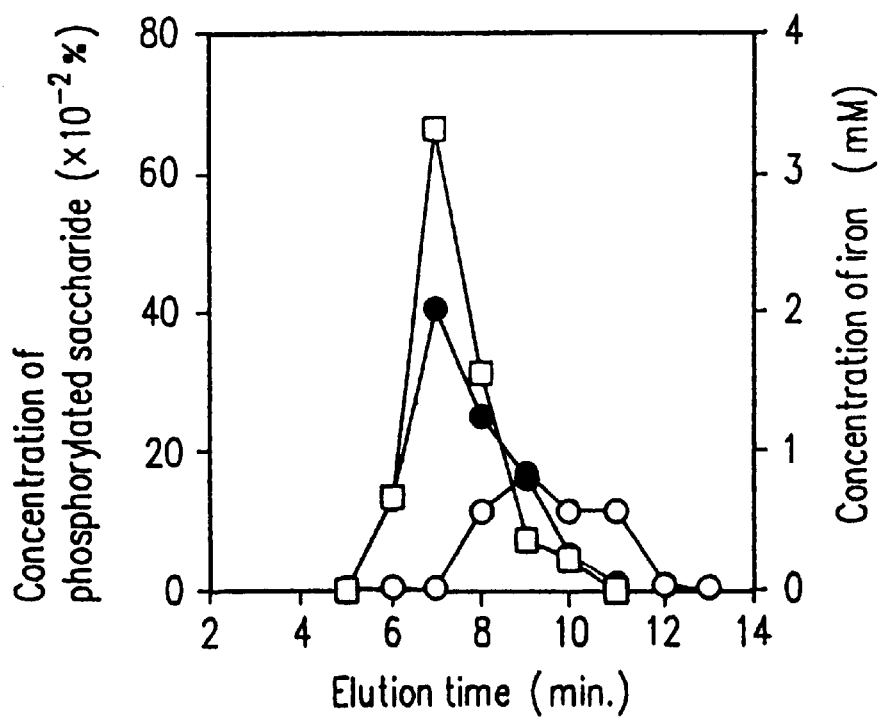
FIG. 2 is a graph showing a gel filtration elution pattern of a phosphorylated saccharide solution and a ferrous chloride solution obtained in Example 1 of the present invention.

FIG. 2 shows gel filtration elution patterns of the following three kinds of solutions: 100 μl of solution of 10% phosphorylated saccharide in Example 1 (an eluate was measured by the concentration of the phosphorylated saccharide; represented by □ in the figure); 100 μl of solution of 100 mM ferrous chloride when being subjected to filtration together with 100 μl of 10% phosphorylated saccharide in Example 1 (an eluate was measured by the concentration of iron; represented by ● in the figure); and 100 μl of solution of 100 mM ferrous chloride (an eluate was measured by the concentration of iron; represented by ○ in the figure). In FIG. 2, the horizontal axis represents an elution time (minutes), the left and right vertical axes represent the concentration of the phosphorylated saccharide ($\times 10^{-2}$%) and that of iron (mM), respectively.

Figure 3:
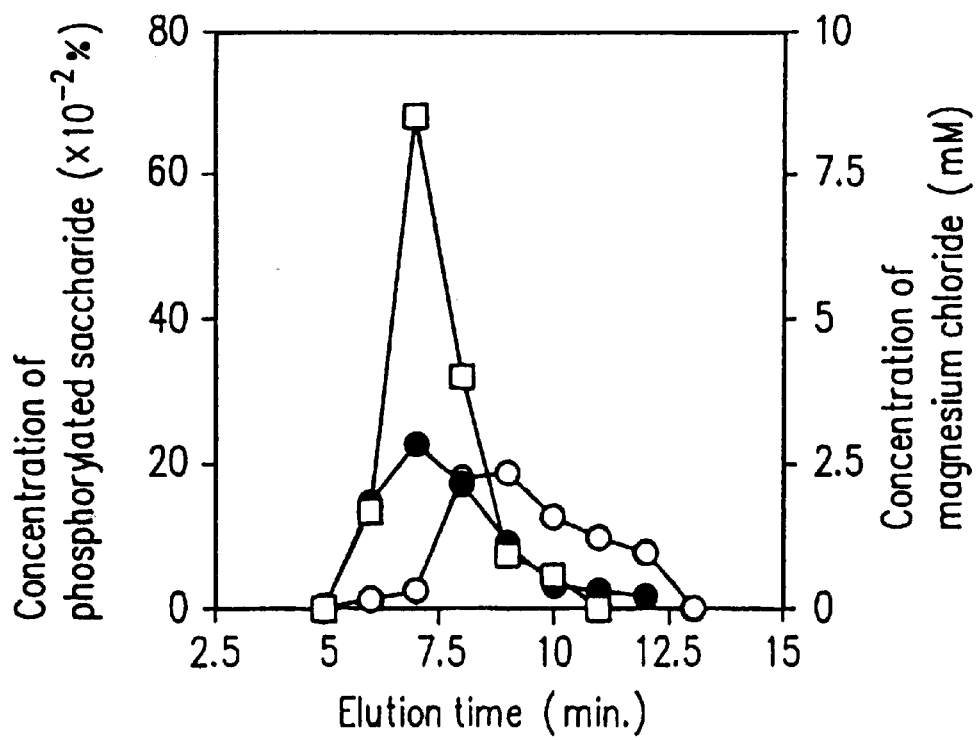
FIG. 3 is a graph showing a gel filtration elution pattern of a phosphorylated saccharide solution and a magnesium chloride solution obtained in Example 1 of the present invention.

FIG. 3 shows gel filtration elution patterns of the following three kinds of solutions: 100 $\mu$l of solution of 10% phosphorylated saccharide in Example 1 (an eluate was measured by the concentration of the phosphorylated saccharide; represented by □ in the figure); 100 $\mu$l of solution of 100 mM magnesium chloride when being subjected to filtration together with 100 $\mu$l of 10% phosphorylated saccharide in Example 1 (an eluate was measured by the concentration of magnesium; represented by ● in the figure); and 100 $\mu$l of solution of 100 mM magnesium chloride (an eluate was measured by the concentration of magnesium; represented by ○ in the figure). In FIG. 3, the horizontal axis represents an elution time (minutes), the left and right vertical axes represent the concentration of the phosphorylated saccharide ($\times 10^{-2}$%) and that of magnesium (mM), respectively.

It was found from the above results that when the phosphorylated saccharide and a metal salt were simultaneously subjected to gel filtration, the elution time of the metal salt was identical with that of the phosphorylated saccharide. The elution time in the case of simultaneously subjecting the metal salt and the phosphorylated saccharide to gel filtration was apparently different from that in the case of subjecting only the metal salt to filtration. Accordingly, in the present example, the ability of forming a compound of the phosphorylated saccharide with calcium, iron, or magnesium was confirmed.

Example 7

First, 20 U of CGTase (produced by Amano pharmaceutical Co., Ltd.) and 30 U of isoamylase (produced by Hayashibara Biochemical Lab.) were added to 1% potato starch dissolved in 5 ml of 10 mM acetate buffer (pH 5.5). The mixture was allowed to react at 40° C. for 14 hours, and was kept in a boiling water bath for 5 minutes to terminate the reaction. The solution thus obtained was centrifuged to obtain a supernatant. Then, 100 mM acetate buffer was added to the supernatant so as to adjust the pH of the supernatant to 4.5. Thereafter, the resulting supernatant was applied to an anion exchange resin column (Chitopearl BCW 2501) equilibrated with the acetate buffer. The column was thoroughly washed with the acetate buffer to remove neutral saccharide, and the resulting supernatant was eluted with the acetate buffer containing 0.5 M sodium chloride. The eluate was desalted and lyophilized to provide phosphorylated saccharide.

Example 8

Figure 4:
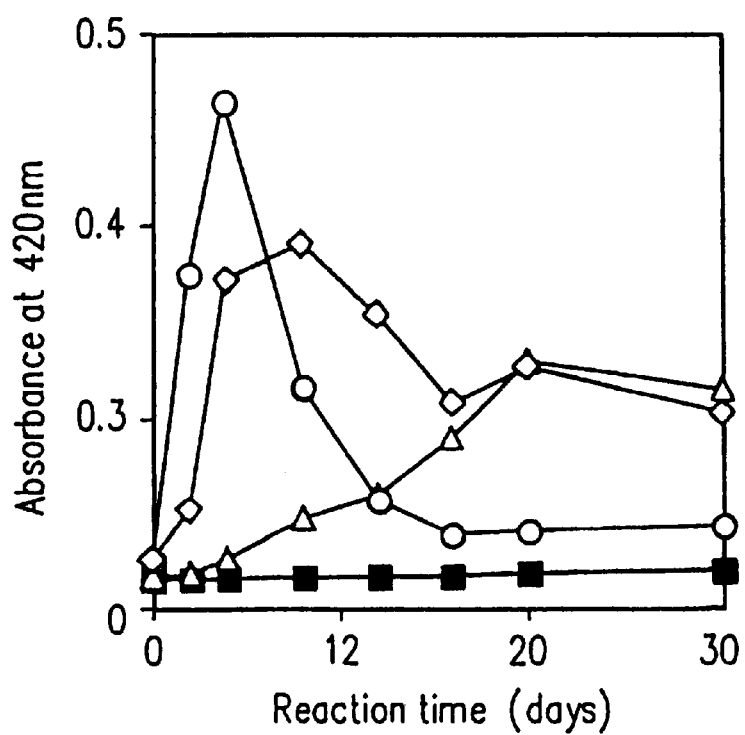
FIG. 4 is a graph showing the degree of progression of a Maillard reaction between various saccharides including phosphorylated saccharide obtained in Example 2 of the present invention and a protein by measuring the absorbance at 420 nm.

A derivative of phosphorylated saccharide with a protein was produced by using the PO-1 fraction obtained in Example 2. First, 1 mg of the PO-1 fraction of Example 2 was mixed with 1 mg of ovalbumin (produced by Sigma Chemical Company) as a protein, and kept at 50° C. under 70% humidity for a predetermined period of time. The pH of the mixture was adjusted to 8. The mixture was sampled on 0th, 2nd, 4th, 8th, 12th, 16th, 20th, and 30th day. The same procedure was also conducted using glucose or glucose-6-phosphate instead of PO-1 fraction of Example 2. After sampling, these samples were respectively dissolved in 1 ml of distilled water and centrifuged to remove precipitates. The degree of pigmentation of each sample was measured at 420 nm as a progress degree of the Maillard reaction. FIG. 4 shows the results.

FIG. 4 shows the results of Maillard reaction between the following saccharide and the protein obtained by measuring the degree of pigmentation at 420 nm: the PO-1 fraction of Example 2 (measured at an absorbance of 420 nm; represented by ◊ in the figure); glucose-6-phosphate (represented by ○ in the figure); glucose (represented by Δ in the figure); and only a protein as a control (represented by ■ in the figure). The horizontal axis represents a reaction time (days) and the vertical axis represents absorbance at 420 nm.

In the case where glucose-6-phosphate was used, the reaction rapidly proceeded to reach a peak in about 4 days, and the product was gradually precipitated. Therefore, the degree of pigmentation of the solution was rapidly decreased. The reaction in the case of using the PO-1 fraction gently proceeded; and that in the case of using glucose more gently proceeded.

Figure 5:
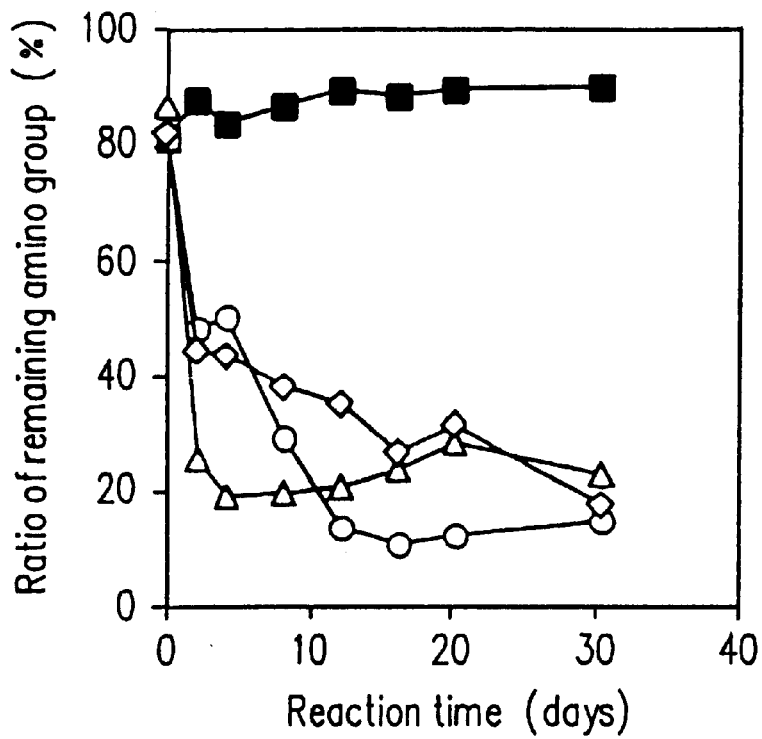
FIG. 5 is a graph showing the degree of progression of a Maillard reaction between various saccharides including phosphorylated saccharide obtained in Example 2 of the present invention and a protein by measuring the ratio of the remaining amino groups by the TNBS method.

The decrease in amino groups was measured as the progress degree of the Maillard reaction by using the TNBS method (Food Engineering Laboratory manual, ed. Department of Food Science and Technology, Faculty of Agriculture, Kyoto University, Yokendo, pp. 620–621, 1982). FIG. 5 shows the results.

FIG. 5 shows the progress degree of the Maillard reaction between the following saccharide and a protein obtained by measuring the decrease in amino groups, using the TNBS method: the PO-1 fraction of Example 2 (the decrease in amino groups was measured by the TNBS method; represented by ◊ in the figure); glucose-6-phosphate (represented by ○ in the figure); glucose (represented by Δ in the figure); and only a protein as a control (represented by ■ in the figure). The horizontal axis represents a reaction time (days) and the vertical axis represents the ratio of the remaining amino groups (%).

As is understood from FIG. 5, the same results as those of FIG. 4 were obtained.

Example 9

Figure 6:
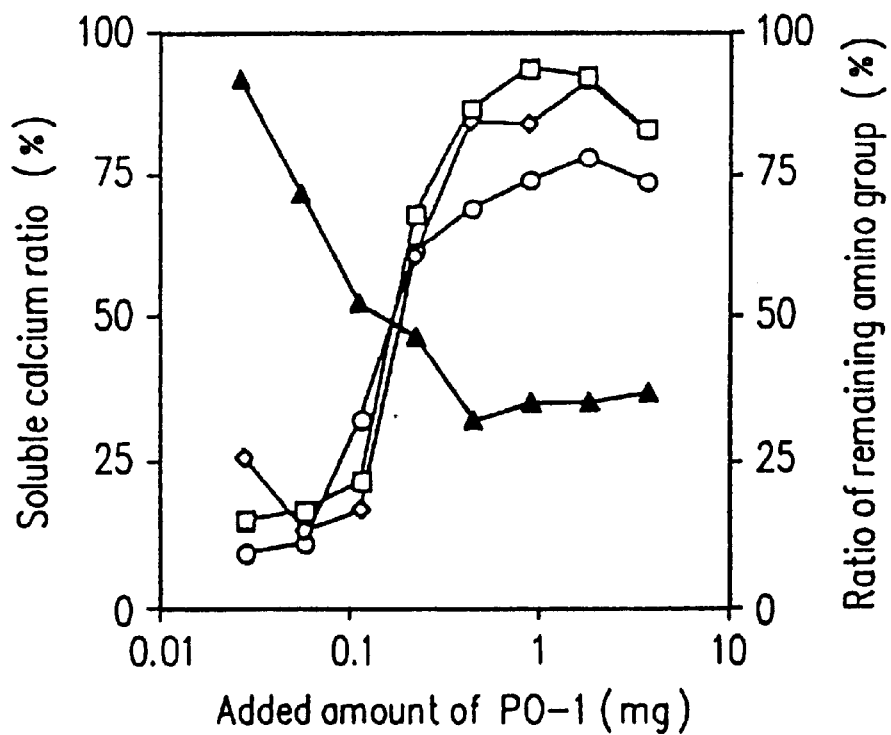
FIG. 6 is a graph showing the calcium solubilization effect of a derivative of the phosphorylated saccharide with a protein obtained in a Maillard reaction in Example 9 of the present invention.
Figure 7:
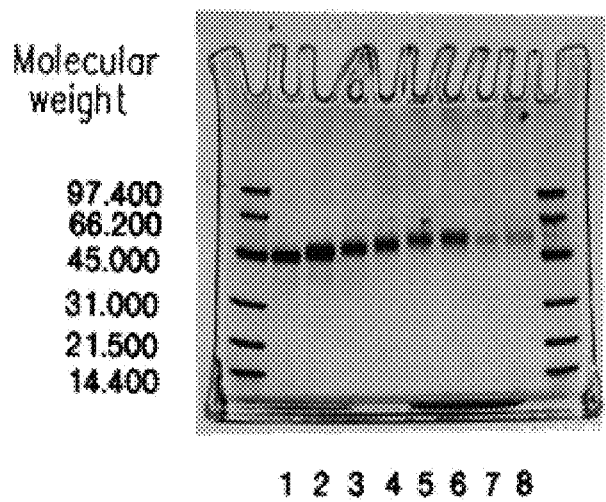
FIG. 7 is an electrophoretogram showing the change in molecular weight of a protein in a Maillard reaction in Example 9 of the present invention.

The Maillard reaction was effected between ovalbumin and the PO-1 fraction, varying the concentration of the PO-1 fraction. Specifically, 1 mg of ovalbumin was mixed with 4 mg, 2 mg, 1 mg, 0.5 mg, 0.25 mg, 0.125 mg, 0.0625 mg, 0.03125 mg, and 0 mg of the PO-1 fractions, respectively. These mixtures were kept for 7 days in accordance with the method of Example 8. Thereafter, the calcium solubilization effect was evaluated. FIG. 6 shows the results. The horizontal axis represents the amount of PO-1 added in the reaction (mg), and the left vertical axis represents a percentage of soluble calcium (represented as a soluble calcium ratio (%) in the figure; the same expression will be used in the other figures). In FIG. 6, □ represents the soluble calcium ratio of the PO-1 fraction after 1 hour; ◊ after 2 hours; and ○ after 4 hours. In this figure, the soluble calcium ratio when the added amount of the PO-1 fraction was 0 mg is not shown. In a similar manner to the above, the decrease in amino groups during the reaction is represented by the right vertical axis as a percentage of the remaining amount of the amino groups (in the figure, ▲ represents TNBS %). As the amino groups decreased and the reaction proceeded, the calcium solubilization effect was exhibited. Furthermore, it is understood from an SDS-polyacrylamide gel electrophoretogram of FIG. 7 that as the reaction proceeded, the molecular weight of the protein was increased. The SDS-polyacrylamide gel electrophoresis was conducted by the method of Laemmli et al. (Nature, vol. 227, pp. 3831–3839, 1970). In FIG. 7, lanes at both ends represent a molecular weight marker. The added amount of the PO-1 fraction in each lane is as follows: 0 mg in Lane 1; 0.0625 mg in Lane 2; 0.125 mg in Lane 3; 0.25 mg in Lane 4; 0.5 mg in Lane 5; 1 mg in Lane 6; 2 mg in Lane 7; and 4 mg in Lane 8. The following was found from FIGS. 6 and 7: it was most effective that 1 mg of the PO-1 fraction was added to 1 mg of ovalbumin; and even if the amount of the PO-1 fraction added was more than 1 mg, the amount of the bound PO-1 fraction was not increased.

Example 10

First, 5 µl of 10 U/ml CGTase (Produced by Amano pharmaceutical Co., Ltd.) was added to 25 µl of 10% phosphorylated saccharide of Example 1 and allowed to react at 37° C. for 15 hours. As a result, a fraction (hereinafter, referred to a PO-2 like fraction) similar to the PO-2 fraction was generated from the PO-1 fraction of Example 2. The PO-2 like fraction is different from the PO-2 fraction of Example 2 obtained from potato starch. This will be described below.

The PO-2 fraction of Example 2 hardly contains phosphate groups bound to glucose at the 6-position, and has a structure in which 2 phosphate groups are bound to oligosaccharide having a degree of polymerization of 2 to 8. However, in a product generated in Example 10, oligosaccharide having a degree of polymerization of 4 or 5 of the PO-1 fraction disappeared or decreased by transfer in the PO-1 fraction caused by CGTase (phosphorylated saccharide having a degree of polymerization of 3 was not transferred), and changed to phosphorylated saccharide with two or more phosphate groups having a higher degree of polymerization.

This was determined as a result of the analysis of the product in accordance with the above-mentioned method for determining structure. It is noted that the product (exhibiting a peak in liquid chromatography at a position similar to that exhibited by the PO-2 fraction) is hardly dephosphorylated with phosphatase under the same conditions and has resistance against phosphatase. Nonetheless, neutral saccharide having a degree of polymerization of up to about 10 was detected, confirming that the PO-2 like fraction was different from the PO-2 fraction obtained in Example 2.

Example 11

Mannan bound by phosphate groups was prepared from yeast by a method of Jeanes et al. (Arch. Biochem. Biophys., vol. 92, pp. 343–350, 1961). Five grams of phosphorylated mannan (containing 4% bound phosphoric acid) were obtained.

Example 12

The calcium solubilization effect was examined in the formation of the compound of the phosphorylated saccharide with calcium.

The calcium solubilization effect was confirmed by inspecting the effect of inhibiting the precipitate formation between calcium saccharide and inorganic phosphate, using a modified method of Yamamoto et al. (Biosci. Biotech. Biochem., vol. 56, pp. 90–93, 1992).

Specifically, 500 µl of 20 mM phosphate buffer (pH 7.4) containing 6 mM sodium azide and 80 mM potassium chloride was thoroughly mixed with 100 µl of test solution or distilled water. Then, 400 µl of 10 mM potassium chloride solution was added to the mixture. The resulting mixture was shaken at 30° C. for 0.5, 1, 2, and 4 hours, respectively; thereafter, the mixture was centrifuged at 10,000 rpm for one minute, and the concentration of calcium in the supernatant was measured by atomic absorption spectroscopy.

Figure 8:
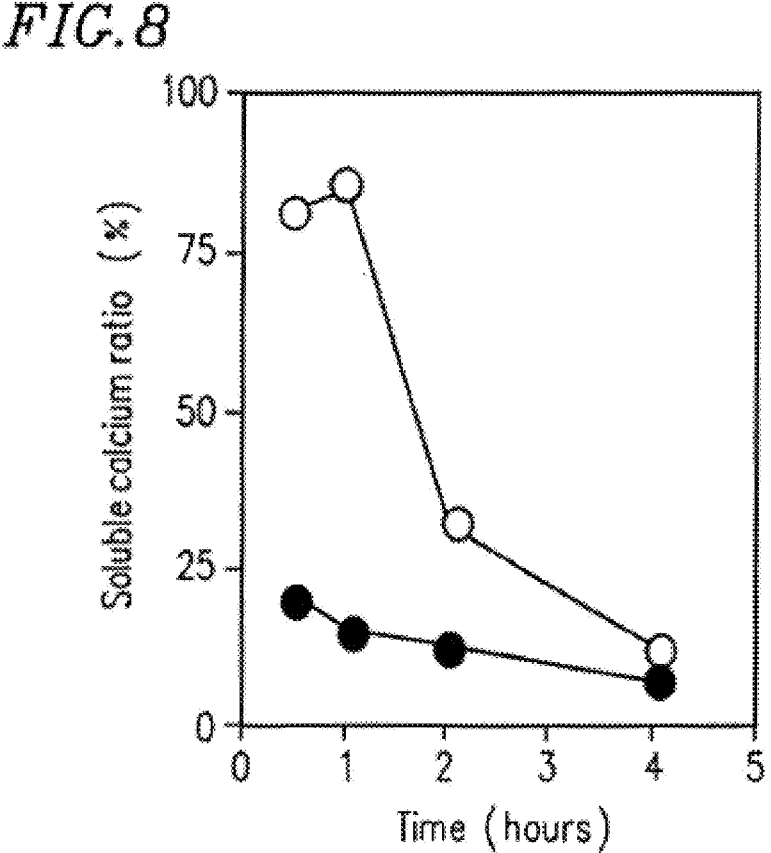
FIG. 8 is a graph showing the calcium solubilization effect of phosphorylated saccharide obtained in Example 1 of the present invention.
Figure 9:
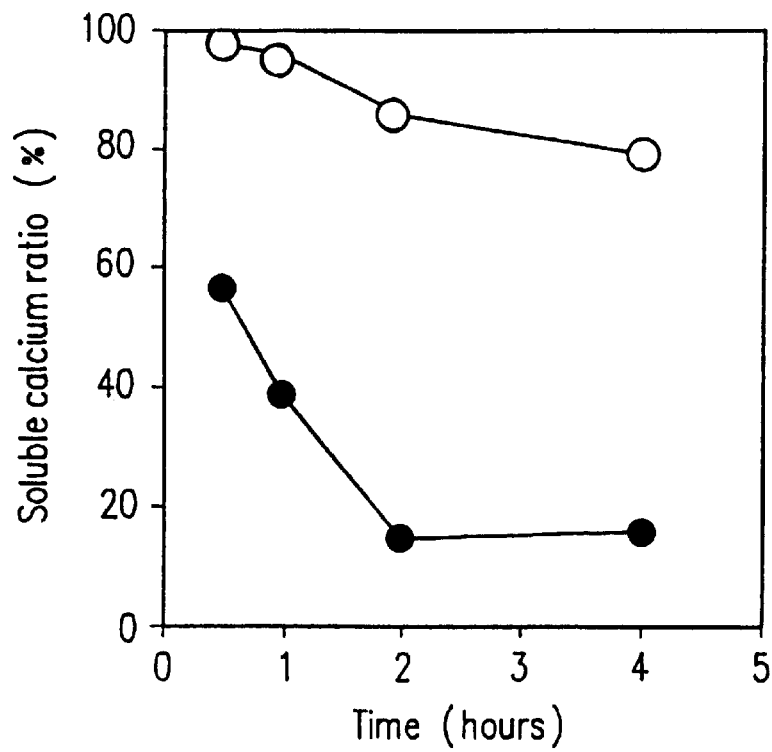
FIG. 9 is a graph showing the calcium solubilization effect of phosphorylated saccharide obtained in Example 2, in which one phosphate group is bound to glucan having a degree of polymerization of 3 to 5 and of phosphorylated saccharide obtained therein in which two or more phosphate groups are bound to glucan having a degree of polymerization of 2 to 8.
Figure 10:
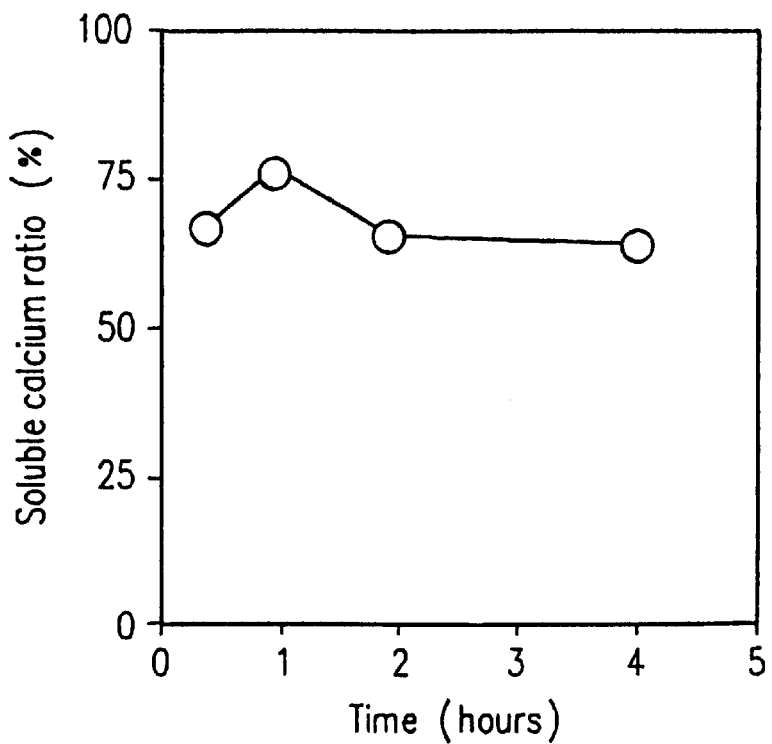
FIG. 10 is a graph showing the calcium solubilization effect of phosphorylated saccharide obtained in Example 4 of the present invention.
Figure 11:
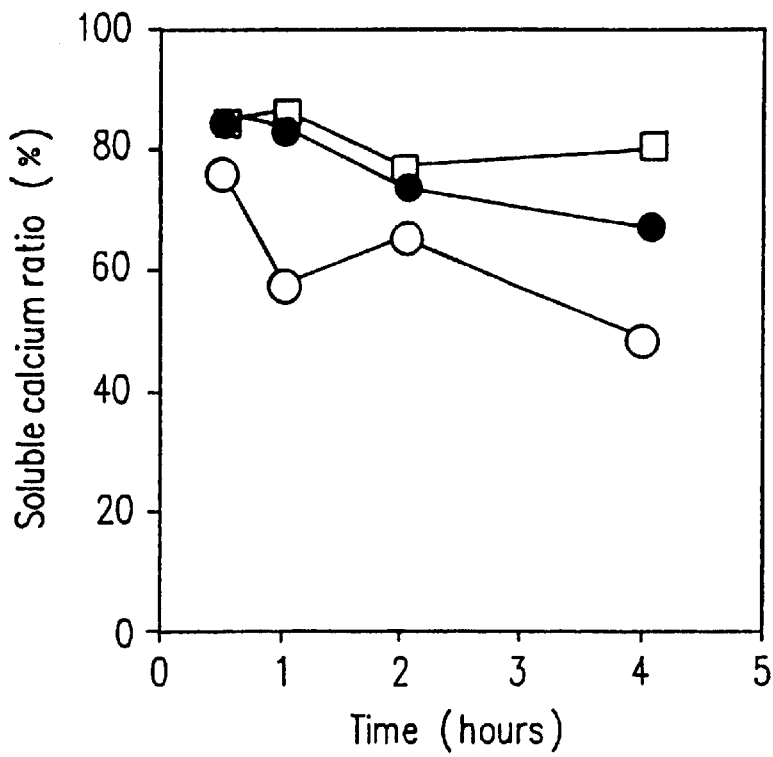
FIG. 11 is a graph showing the calcium solubilization effect of sodium alginate, pectin, and CPP.
Figure 12:
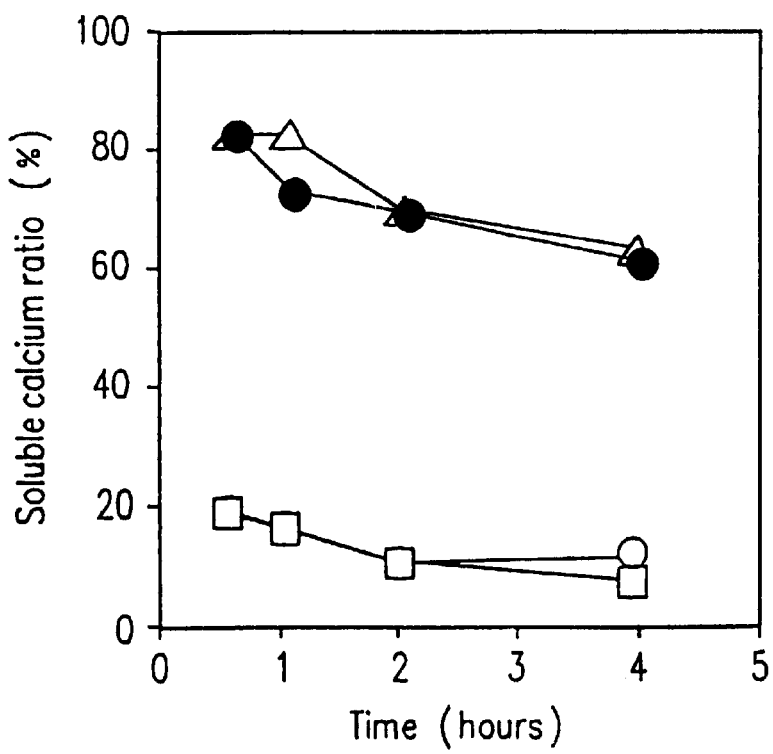
FIG. 12 is a graph showing the calcium solubilization effect of fructose-1,6-diphosphate, glucose-6-phosphate, fructose-6-phosphate, and glucose-1,6-diphosphate.

FIG. 8 shows the case of using the phosphorylated saccharide obtained in Example 1 as a test solution. FIG. 9 shows the case of using the phosphorylated saccharide with one phosphate group bound to α-1,4-glucan having a degree of polymerization of 3 to 5 obtained in Example 2 and the phosphorylated saccharide with two or more phosphate groups bound to α-1,4-glucan having a degree of polymerization of 2 to 8 obtained in Example 2. FIG. 10 shows the case of using the phosphorylated saccharide obtained in Example 4. FIG. 11 shows the case of using casein phosphopeptide (CPPIII; produced by Meiji Seika Kaisha Ltd.) and pectin and sodium alginate. FIG. 12 shows the case of using glucose-1,6-diphosphate, glucose-6-phosphate, fructose-1,6-diphosphate, and fructose-6-phosphate. In these figures, the horizontal axis represents a shaking time (hours) and the vertical axis represents a soluble calcium ratio (%).

In FIG. 8, 100 µl each of 1% phosphorylated saccharide (represented by ● in the figure) and 5% phosphorylated saccharide (represented by ○ in the figure) obtained in Example 1 was independently mixed with 500 µl of 20 mM phosphate buffer (pH 7.4) containing 6 mM sodium azide and 80 mM potassium chloride. Then, 400 µl of 10 mM calcium chloride solution was added to the mixture. The resulting mixture was shaken at 30° C. for 0.5, 1, 2, and 4 hours, respectively; thereafter, the mixture was centrifuged at 10,000 rpm for one minute, and the concentration of calcium in the supernatant was measured by atomic absorption spectroscopy.

In FIG. 9, 100 µl each of 5% phosphorylated saccharide (represented by ● in the figure) with one phosphate group bound to α-1,4-glucan containing 3 to 5 glucoses and 5% phosphorylated saccharide (represented by ○ in the figure) with two or more phosphate groups bound to α-1,4 -glucan containing 2 to 8 glucoses obtained in Example 2 was independently mixed with 500 µl of 20 mM phosphate buffer (pH 7.4) containing 6 mM sodium azide and 80 mM potassium chloride. Then, 400 µl of 10 mM calcium chloride solution was added to the respective mixtures. Each of the resulting mixtures was shaken at 30° C. for 0.5, 1, 2, and 4 hours, respectively; thereafter, the mixture was centrifuged at 10,000 rpm for one minute, and the concentration of calcium in the respective supernatant was measured by atomic absorption spectroscopy.

In FIG. 10, 100 µl of 5% phosphorylated saccharide obtained in Example 4 was thoroughly mixed with 500 µl of 20 mM phosphate buffer (pH 7.4) containing 6 mM sodium azide and 80 mM potassium chloride. Then, 400 µl of 10 mM calcium chloride solution was added to the mixture. The resulting mixture was shaken at 30° C. for 0.5, 1, 2, and 4 hours, respectively; thereafter, the mixture was centrifuged at 10,000 rpm for one minute, and the concentration of calcium in the supernatant was measured by atomic absorption spectroscopy.

In FIG. 11, 100 µl each of 5% sodium alginate (represented by □ in the figure), 5% pectin (represented by ● in the figure), and 5% CPPIII (produced by Meiji Seika) (represented by ○ in the figure) was independently mixed with 500 µl of 20 mM phosphate buffer (pH 7.4) containing 6 mM sodium azide and 80 mM potassium chloride. Then, 400 μl of 10 mM calcium chloride solution was added to the respective mixtures. Each of the resulting mixtures was shaken at 30° C. for 0.5, 1, 2, and 4 hours, respectively; thereafter, each mixture was centrifuged at 10,000 rpm for one minute, and the concentration of calcium in the respective supernatant was measured by atomic absorption spectroscopy.

In FIG. 12, 100 μl each of 5% fructose-1,6-diphosphate (represented by Δ in the figure), glucose-6-phosphate (represented by □ in the figure), fructose-6-phosphate (represented by ○ in the figure), and glucose-1,6-diphosphate (represented by ● in the figure) was independently mixed with 500 μl of 20 mM phosphate buffer (pH 7.4) containing 6 mM sodium azide and 80 mM potassium chloride. Then, 400 μl of 10 mM calcium chloride solution was added to the mixture. The resulting mixture was shaken at 30° C. for 0.5, 1, 2, and 4 hours, respectively; thereafter, the mixture was centrifuged at 10,000 rpm for one minute, and the concentration of calcium in the supernatant was measured by atomic absorption spectroscopy.

It was made apparent from the above results that the phosphorylated saccharide forms a compound or a complex with calcium, thereby inhibiting the insolubilization of calcium due to the formation of calcium phosphate even in a weak alkali atmosphere which is the same as that in the intestine. Furthermore, this effect was found to be prominent in the phosphorylated saccharide having two or more phosphate groups per molecule and in the phosphorylated saccharide prepared in Example 4.

Example 13

The concentration of each material at which the calcium solubilization effect thereof was exhibited was measured. First, 100 μl each of 0.1%, 0.075%, 0.05%, 0.025%, 0.01%, and 0.005% test solutions was independently mixed with 500 μl of 20 mM phosphate buffer (pH 7.4) containing 6 mM sodium azide and 80 mM potassium chloride. Then, 400 μl of 10 mM calcium chloride solution was added to the mixture. The resulting mixture was shaken at 30° C. for 2 hours; thereafter, the mixture was centrifuged at 10,000 rpm for one minute, and the concentration of calcium in the supernatant was measured by atomic absorption spectroscopy.

Figure 13:
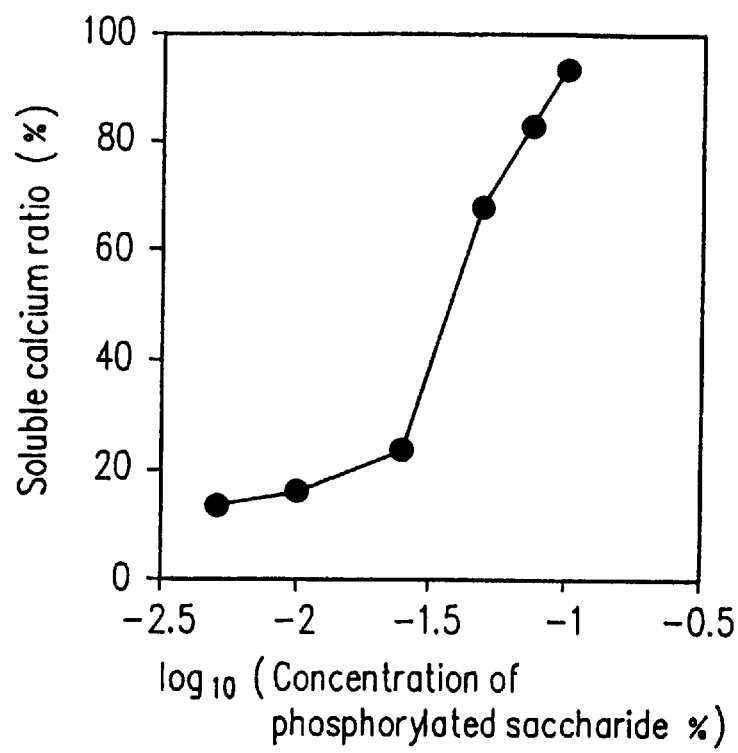
FIG. 13 is a graph showing the calcium solubilization effect of phosphorylated saccharide in various concentrations in which two or more phosphate groups are bound to glucan having a degree of polymerization of 2 to 8 obtained in Example 2 of the present invention.
Figure 14:
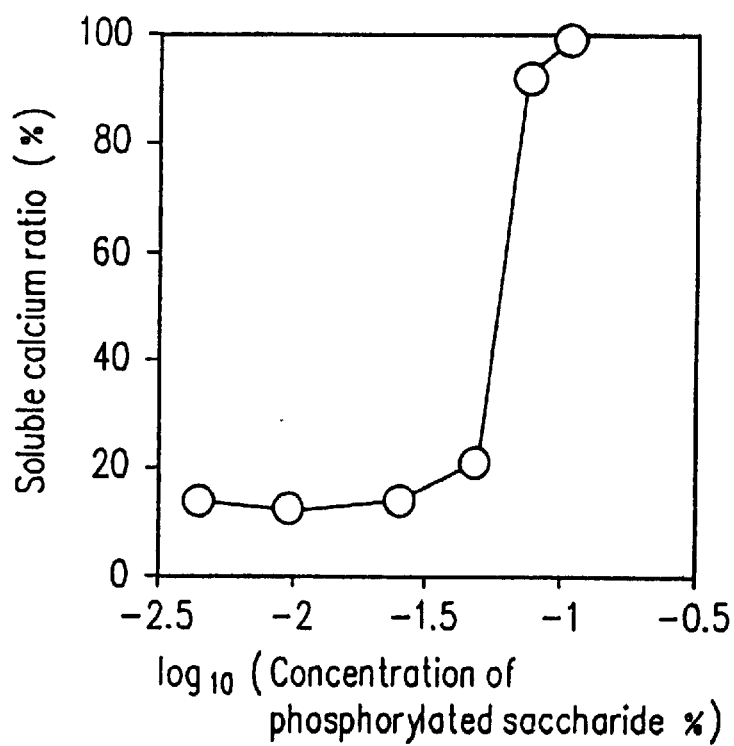
FIG. 14 is a graph showing the calcium solubilization effect of phosphorylated saccharide in various concentrations obtained in Example 4 of the present invention.
Figure 15:
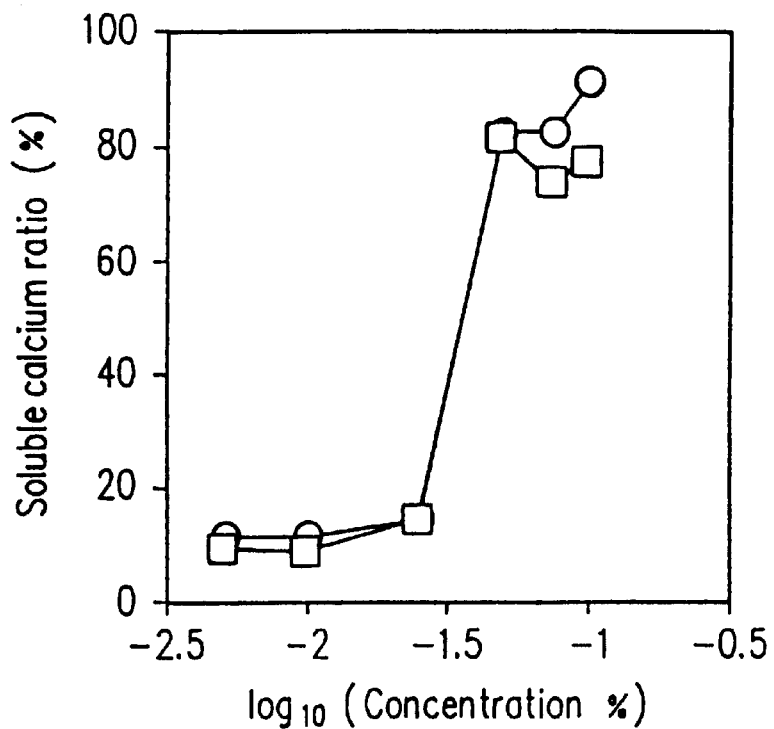
FIG. 15 is a graph showing the calcium solubilization effect of sodium alginate and casein phosphopeptide respectively in various concentrations.

FIG. 13 shows the case of using the phosphorylated saccharide with two or more phosphate groups bound to glucan having a degree of polymerization of 2 to 8 obtained in Example 2 as a test solution. FIG. 14 shows the case of using the phosphorylated saccharide obtained in Example 4. FIG. 15 shows the case of using casein phosphopeptide (CPPIII; produced by Meiji Seika Kaisha Ltd.) (represented by □ in the figure) or sodium alginate (represented by ○ in the figure). The horizontal axis represents the concentration of phosphorylated saccharide expressed in common logarithm and the vertical axis represents the soluble calcium ratio (%).

Example 14

The concentration of glucose-1,6-diphosphate, fructose-1,6-diphosphate, and glucose-6-phosphate at which the calcium solubilization effect thereof was exhibited was measured.

Figure 16:
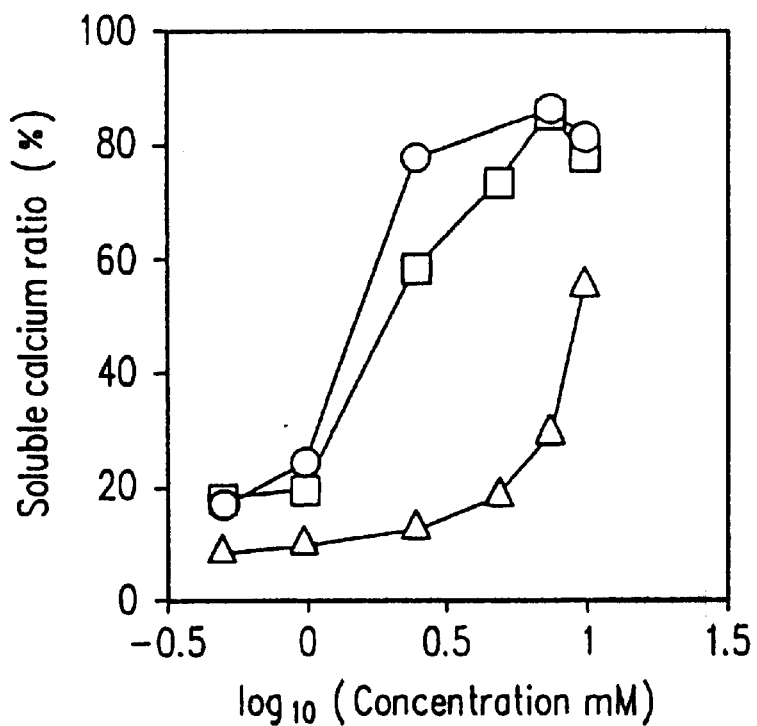
FIG. 16 is a graph showing the calcium solubilization effect of fructose-1,6-diphosphate, glucose-6-phosphate, and glucose-1,6-diphosphate in various concentrations.

First, 100 μl each of 10 mM, 7.5 mM, 5 mM, 2.5 mM, 1 mM, and 0.5 mM test solutions was independently mixed with 500 μl of 20 mM phosphate buffer (pH 7.4) containing 6 mM sodium azide and 80 mM potassium chloride. Then, 400 μl of 10 mM calcium chloride solution was added to the mixture. The resulting mixture was shaken at 30° C. for 2 hours; thereafter, the mixture was centrifuged at 10,000 rpm for one minute, and the concentration of calcium in the supernatant was measured by atomic absorption spectroscopy. FIG. 16 shows the results.

In FIG. 16, 100 μl each of fructose-1,6-diphosphate (represented by □ in the figure), glucose-6-phosphate (represented by Δ in the figure), and glucose-1,6-diphosphate (represented by ○ in the figure) each adjusted to 10 mM, 7.5 mM, 5 mM, 2.5 mM, 1 mM, and 0.5 mM was independently mixed with 500 μl of 20 mM phosphate buffer (pH 7.4) containing 6 mM sodium azide and 80 mM potassium chloride. Then, 400 μl of 10 mM calcium chloride solution was added to the mixture. The resulting mixture was shaken at 30° C. for 2 hours; thereafter, the mixture was centrifuged at 10,000 rpm for one minute, and the concentration of calcium in the supernatant was measured by atomic absorption spectroscopy. The horizontal axis represents the concentration of the test solutions expressed in common logarithm and the vertical axis represents the soluble calcium ratio (%).

It was found from Examples 12, 13 and 14 that the calcium solubilization effect of the phosphorylated saccharide of the present invention has the same level as that of casein phosphopeptide and alginate.

Example 15

Figure 17:
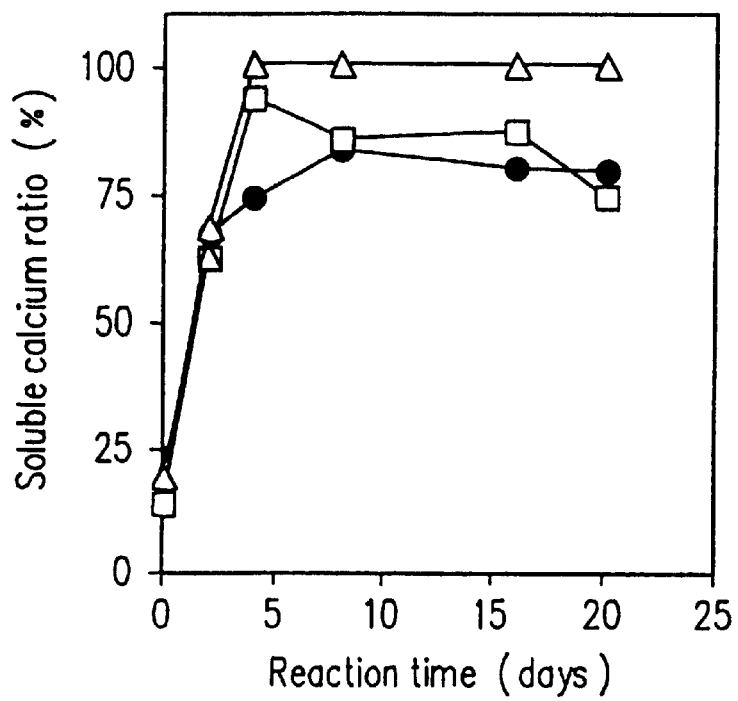
FIG. 17 is a graph showing the calcium solubilization effect of a derivative obtained from phosphorylated saccharide obtained in Example 2 (PO-1) and a protein.
Figure 18:
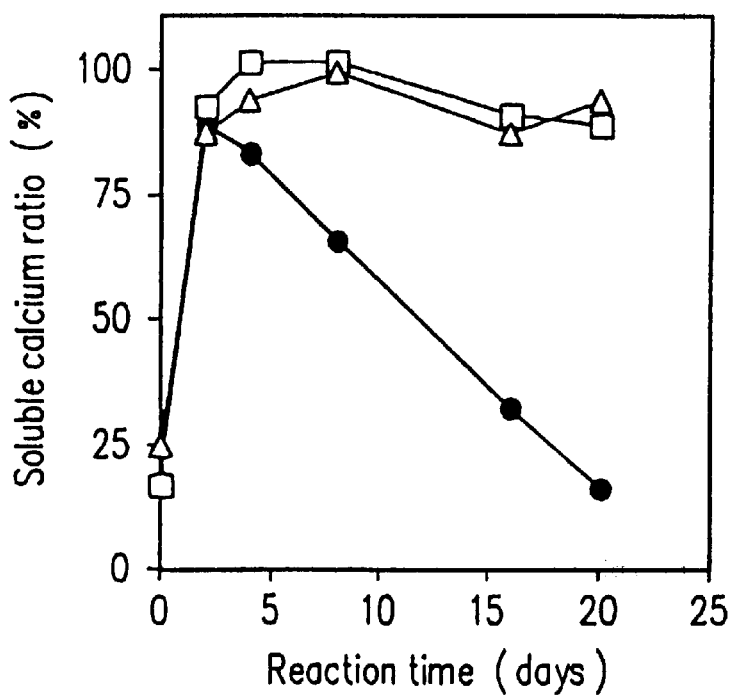
FIG. 18 is a graph showing the calcium solubilization effect of a derivative obtained from glucose-6-phosphate and a protein.
Figure 19:
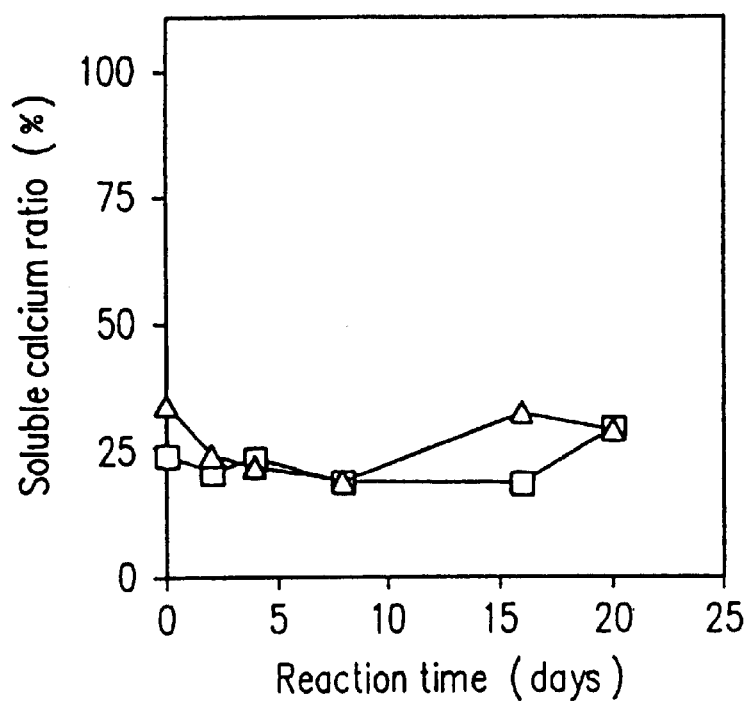
FIG. 19 is a graph showing the calcium solubilization effect of a derivative obtained from glucose and a protein.

The calcium solubilization effect of the derivative of the phosphorylated saccharide with a protein obtained in Example 8 was examined. FIGS. 17, 18, and 19 show the results. In these figures, the horizontal axis represents a reaction time (days) and the vertical axis represents a soluble calcium ratio (%).

In FIG. 17, 100 μl of 1% product obtained by the Maillard reaction between the PO-1 fraction of Example 2 and a protein shown in FIG. 4 was mixed with 500 μl of 20 mM phosphate buffer (pH 7.4) containing 6 mM sodium azide and 80 mM potassium chloride. Then, 400 μl of 10 mM calcium chloride solution was added to the mixture. The resulting mixture was shaken at 30° C. for 0.5 hours (represented by Δ in the figure), 1 hour (represented by □ in the figure), and 4 hours (represented by ● in the figure) and centrifuged at 10,000 rpm for one minute. The concentration of calcium in the supernatant was measured by atomic absorption spectroscopy.

In FIG. 18, 100 μl of 1% product obtained by the Maillard reaction between glucose-6-phosphate and a protein shown in FIG. 4 was mixed with 500 μl of 20 mM phosphate buffer (pH 7.4) containing 6 mM sodium azide and 80 mM potassium chloride. Then, 400 μl of 10 mM calcium chloride solution was added to the mixture. The resulting mixture was shaken at 30° C. for 0.5 hours (represented by Δ in the figure), 1 hour (represented by □ in the figure), and 4 hours (represented by ● in the figure) and centrifuged at 10,000 rpm for one minute. The concentration of calcium in the supernatant was measured by atomic absorption spectroscopy.

In FIG. 19, 100 μl of 1% product obtained by the Maillard reaction between glucose and a protein shown in FIG. 4 was mixed with 500 μl of 20 mM phosphate buffer (pH 7.4) containing 6 mM sodium azide and 80 mM potassium chloride. Then, 400 μl of 10 mM calcium chloride solution was added to the mixture. The resulting mixture was shaken at 30° C. for 0.5 hours (represented by Δ in the figure), 1 hour (represented by □ in the figure), and 4 hours (represented by ● in the figure) and centrifuged at 10,000 rpm for one minute. The concentration of calcium in the supernatant was measured by atomic absorption spectroscopy.

The phosphorylated saccharide of the PO-1 fraction of Example 2 itself had a weak calcium solubilization effect; however, when a plurality of phosphorylated saccharides were bound to a protein, they gained a stronger calcium solubilization. The solubilization effect of a derivative of glucose-6-phosphate with a protein generally disappears 2 hours later. The phosphorylated saccharide derivative of the present invention was found to stably exhibit a solubilization effect. The derivative of glucose with a protein did not exhibit a calcium solubilization effect. Thus, it was found that it was required to use saccharides bound by phosphate groups for obtaining a calcium solubilization effect.

Example 16

Figure 20:
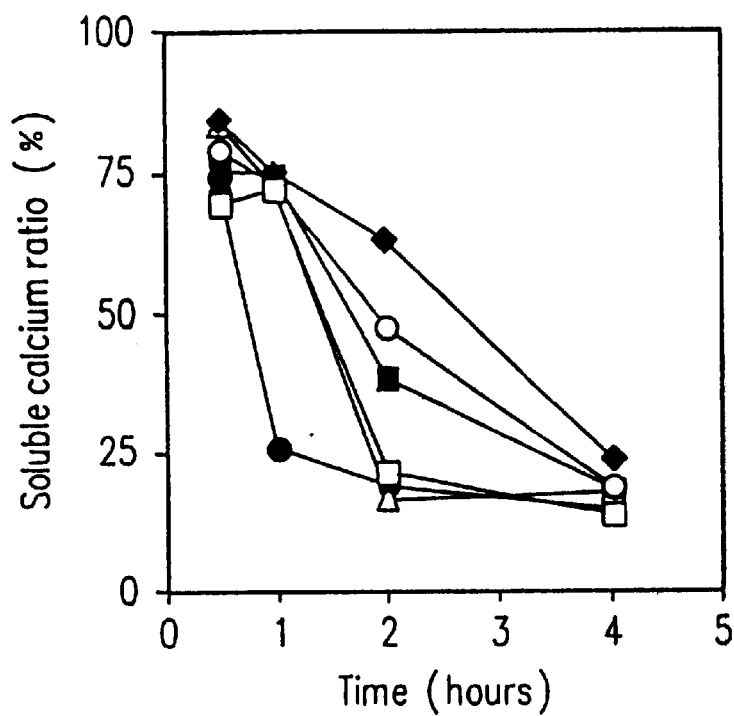
FIG. 20 is a graph showing the calcium solubilization effect of phosphorylated saccharide of Example 10 of the present invention.

In Example 10, first, 5 μl of 10 U/ml CGTase dissolved in 60 mM acetate buffer was added to 25 μl of 10% phosphorylated saccharide of Example 1. The mixture was allowed to react at 37° C. for 15 hours; as a result, a PO-2 like fraction was found to be generated from the PO-1 fraction of Example 2. The calcium solubilization effect of the phosphorylated saccharide of Example 10 was examined. FIG. 20 shows the results. In this figure, the horizontal axis represents a reaction time (hours), and the vertical axis represents a soluble calcium ratio (%). In FIG. 20, the following CGTases were used: that derived from *Bacillus thermophilic* (represented by □ in the figure); that derived from *Bacillus circulans* (represented by ♦ in the figure); that derived from *Bacillus megaterium* (represented by ○ in the figure); commercially available *Bacillus macerans* (represented by Δ in the figure); Alkaline CGTase (T. Kometani et al., Biosci. Biotech. Biochem., vol. 58, pp. 517–520, 1994) (represented by ■ in the figure); and 60 mM acetate buffer as a control (represented by ● in the figure). Next, 100 μl of 1% phosphorylated saccharide was mixed with 500 μl of 20 mM phosphate buffer (pH 7.4) containing 6 mM sodium azide and 80 mM potassium chloride. Then, 400 μl of 10 mM calcium chloride solution was added to the mixture; thereafter, the resulting mixture was shaken at 30° C. for 0.5, 1, 2, and 4 hours and centrifuged at 10,000 rpm for one minute, and the concentration of calcium in the supernatant was measured by atomic absorption spectroscopy.

The PO-2 like fraction also increased the calcium solubilization effect. It is considered that this is because two or more phosphate groups are present in one molecule.

Example 17

Figure 21:
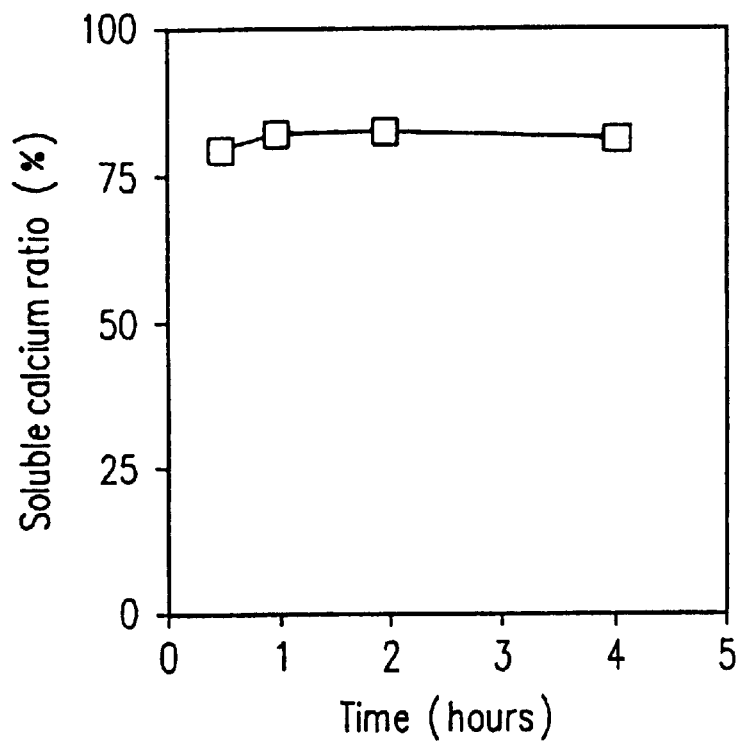
FIG. 21 is a graph showing the calcium solubilization effect of phosphorylated saccharide composed of mannose prepared from yeast.

The calcium solubilization effect of the phosphorylated saccharide composed of mannose in Example 11 was examined. FIG. 21 shows the results. In this figure, the horizontal axis represents a reaction time (hours) and the vertical axis represents a soluble calcium ratio (%). First, 100 μl of 1% phosphorylated saccharide was mixed with 500 μl of 20 mM phosphate buffer (pH 7.4) containing 6 mM sodium azide and 80 mM potassium chloride. Then, 400 μl of 10 mM calcium chloride solution was added to the mixture. The resulting mixture was shaken at 30° C. for 0. 5, 1, 2, and 4 hours and centrifuged at 10,000 rpm for one minute. The concentration of calcium in the supernatant was measured by atomic absorption spectroscopy. It was found from the present example that the calcium solubilization effect was exhibited irrespective of the constituent saccharide of phosphorylated saccharide.

Example 18

First, 100 μl of 1% phosphorylated saccharide of Example 1 was independently mixed with 200 μl each of 0.5 mM, 1 mM, 5 mM, and 10 mM metal chloride solution. Then, 500 μl of ethanol was added to the respective mixtures and the presence or absence of precipitates to be generated was visually compared. Table 1 shows the results. Furthermore, 500 μl of ethanol was added to the respective mixtures and comparison was made in a similar manner. Table 2 shows the results.

Figure 22:
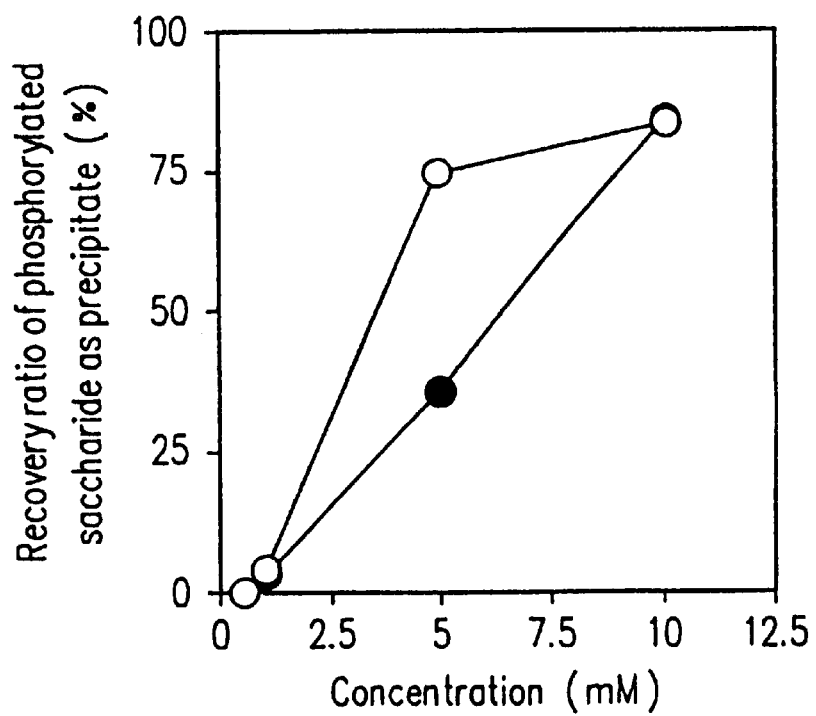
FIG. 22 is a graph showing the recovery ratio of the phosphorylated saccharide of Example 1 of the present invention when calcium chloride or ferrous chloride is added thereto.

FIG. 22 shows the recovery ratio of phosphorylated saccharide when calcium chloride (represented by ○ in the figure) or ferrous chloride (represented by ● in the figure) were added. In this figure, the horizontal axis represents the concentration of each metal salt (mM), and the vertical axis represents the recovery ratio of phosphorylated saccharide as a precipitate (%).

TABLE 1

| Kind of metal chloride | 0.5 mM | 1 mM | 5 mM | 10 mM |
|---|---|---|---|---|
| Sodium | − | − | − | − |
| Potassium | − | − | − | − |
| Ammonium | − | − | − | − |
| Magnesium | − | − | − | + |
| Calcium | − | − | ++ | +++ |
| Barium | − | − | ++ | +++ |
| Copper (II) | − | − | + | + |
| Zinc | − | − | + | ++ |
| Manganese (II) | − | − | + | ++ |
| Iron (II) | − | − | + | +++ |
| Iron (III) | − | − | +++ | − |
| Cobalt (II) | − | − | + | ++ |
| Nickel | − | − | + | ++ |
| Cadmium | − | − | + | +++ |
| Strontium | − | − | ++ | +++ |
| Distilled water | − | − | − | − |

Notes: − Precipitation was not recognized.
+ Precipitation was slightly recognized.
++ Precipitation was recognized.
+++ Precipitation was remarkably recognized.

TABLE 2

| Kind of metal chloride | 0.5 mM | 1 mM | 5 mM | 10 mM |
|---|---|---|---|---|
| Sodium | + | + | ++ | +++ |
| Potassium | + | + | ++ | +++ |
| Ammonium | − | − | − | − |
| Magnesium | + | + | ++ | +++ |
| Calcium | ++ | +++ | +++ | ++ |
| Barium | + | + | +++ | +++ |
| Copper (II) | + | + | + | + |
| Zinc | + | + | +++ | +++ |
| Manganese (II) | + | + | +++ | +++ |
| Iron (II) | + | + | ++ | +++ |
| Iron (III) | − | − | +++ | ++ |
| Cobalt (II) | − | − | ++ | ++ |
| Nickel | − | − | ++ | +++ |
| Cadmium | + | + | ++ | +++ |

TABLE 2-continued

| Kind of metal chloride | 0.5 mM | 1 mM | 5 mM | 10 mM |
|---|---|---|---|---|
| Strontium | + | + | ++ | +++ |
| Distilled water | − | − | − | − |

Notes: − Precipitation was not recognized.
+ Precipitation was slightly recognized.
++ Precipitation was recognized.
+++ Precipitation was remarkably recognized.

Example 19

Figure 23:
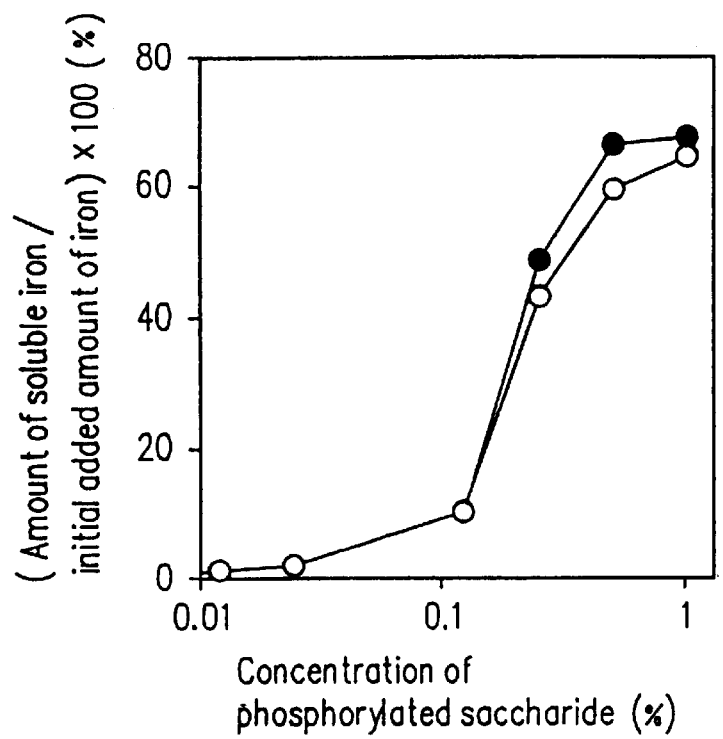
FIG. 23 is a graph showing the iron ion solubilization effect when the phosphorylated saccharide of Example 1 of the present invention is added to ferrous chloride.
Figure 24:
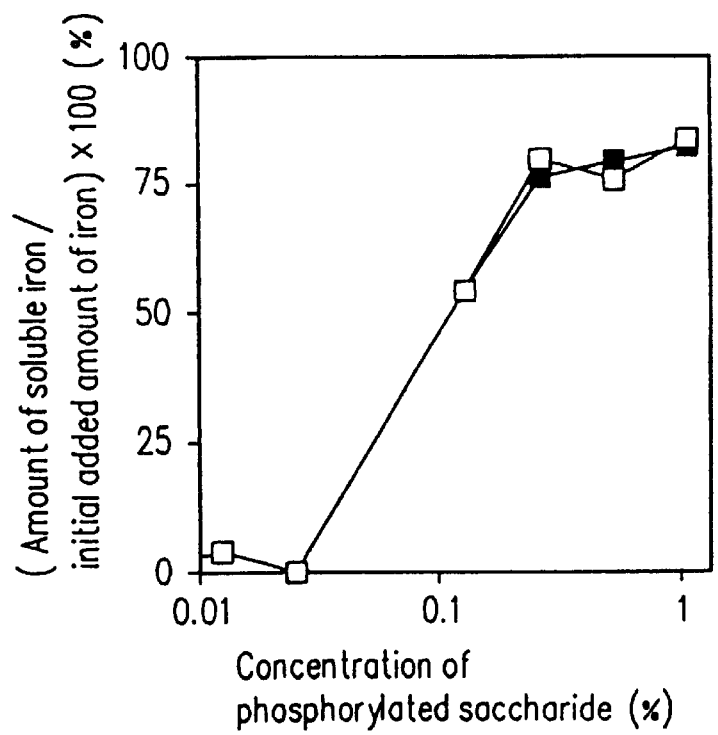
FIG. 24 is a graph showing the iron ion solubilization effect when the phosphorylated saccharide of Example 1 of the present invention is added to ferric chloride.

The chelate effect of iron was examined in accordance with a method of Kawakami et al. (Biosci. Biotech. Biochem. vol. 57, pp. 1376–1377, 1993). Specifically, the phosphorylated saccharide of Example 1 was added to 25 μl of 100 mM ferrous chloride so that the final concentration of the phosphorylated saccharide became 0%, 0.0125%, 0.025%, 0.125%, 0.25%, 0.5%, and 1%. Similarly, the phosphorylated saccharide of Example 1 was added to 25 μl of 100 mM ferric chloride so that the final concentration of the phosphorylated saccharide became 0%, 0.0125%, 0.025%, 0.125%, 0.25%, 0.5%, and 1%. Then, 200 mM sodium carbonate was added to each solution so as to adjust the pH to 7. Furthermore, distilled water was added to each of the resulting solutions to give 1 ml of each solution. These solutions were shaken at 37° C. for 24 and 48 hours and centrifuged. The iron concentration of each supernatant of the solutions was measured by atomic absorption spectroscopy. FIGS. 23 and 24 show the results. In these figures, the horizontal axis represents the concentration of phosphorylated saccharide (%), and the vertical axis represents the percentage of the amount of soluble iron to the initial amount of added iron (%).

In FIG. 23, the phosphorylated saccharide was added to 25 μl of 100 mM ferrous chloride so that the final concentration of the phosphorylated saccharide became 0%, 0.0125%, 0.025%, 0.125%, 0.25%, 0.5%, and 1%. Then, 200 mM sodium bicarbonate was added to each solution so as to adjust the pH thereof to 7. Furthermore, distilled water was added to each of the resulting solutions to give 1 ml of each solution. These solutions were shaken at 37° C. for 24 hours (represented by ○ in the figure) and 48 hours (represented by ● in the figure) and centrifuged. The iron concentration of each supernatant was measured by atomic-absorption spectroscopy.

In FIG. 24, the phosphorylated saccharide was added to 25 μl of 100 mM ferric chloride so that the final concentration of the phosphorylated saccharide became 0%, 0.0125%, 0.025%, 0.125%, 0.25%, 0.5%, and 1%. Then, 200 mM sodium bicarbonate was added to each solution so as to adjust the pH to 7. Furthermore, distilled water was added to each of the resulting solutions to give 1 ml of each solution. These solutions were shaken at 37° C. for 24 hours (represented by □ in the figure) and 48 hours (represented by ■ in the figure) and centrifuged. The iron concentration of each supernatant of the solutions was measured by atomic absorption spectroscopy.

It was found from the present example that the phosphorylated saccharide has an effect of solubilizing iron ions at a concentration of about 0.1%.

Example 20

Figure 25:
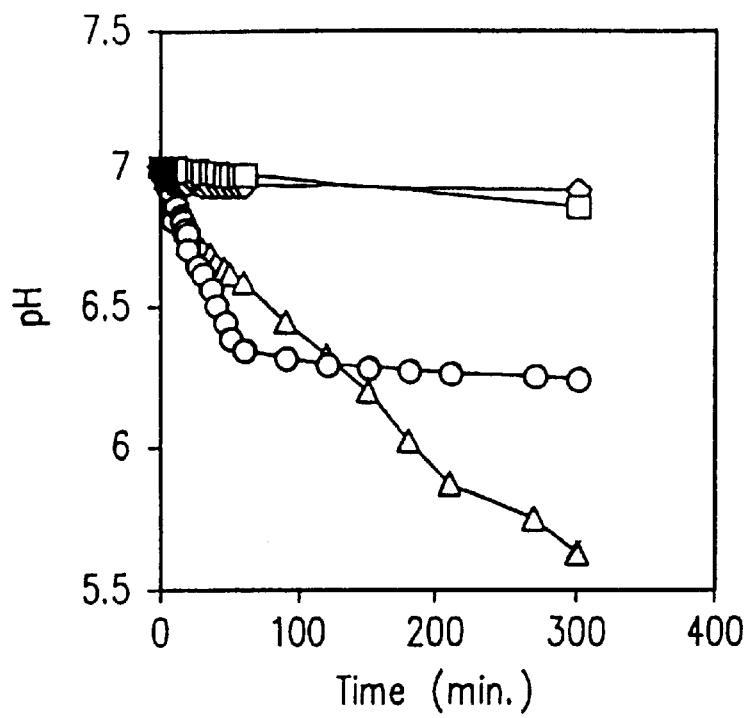
FIG. 25 is a graph showing the results of the acid generation by *Streptococcus mutans* of various saccharides including phosphorylated saccharide of Example 1 of the present invention.

The presence or absence of the acid generation by *Streptococcus mutans* causing dental caries was confirmed. As *Streptococcus mutans*, *S. mutans* strain 6715 was used. The strain was incubated statically at 37° C. for 24 hours in Brain Heart Infusion (produced by DIFCO Corporation); then, 1 liter of the strain was incubated under the same condition. Strain cells were collected by centrifugation and suspended in 10 ml of 100 mM phosphate buffer (pH 7.0) so as to obtain a strain concentration of 0.2 g/ml. Then, 1.5 ml of this solution was mixed with 1.5 ml of 20 mM test saccharide solution, and the mixture was allowed to stand at 37° C. Under this condition, the pH of the solution was measured at established periods. The test saccharide solutions used in the present example were the phosphorylated saccharide of Example 1 (represented by ◇ in the figure), sucrose (represented by ∆ in the figure), maltotriose (represented by □ in the figure), and glucose (represented by ○ in the figure). FIG. 25 shows the results. In the figure, the horizontal axis represents a reaction time (minutes) and the vertical axis represents the change in pH.

It was found in the present example that when the phosphorylated saccharide was used, the pH of the solution was not decreased unlike the case of using sucrose and glucose, and acid was not generated. More specifically, it was found that the phosphorylated saccharide of the present invention did not become a nutrient source for *Streptococcus mutans*.

Example 21

It was confirmed whether or not the phosphorylated saccharide was used as a substrate for enzyme GTase produced by *Streptococcus mutans* causing dental caries to generate glucan. As GTase, that derived from *Streptococcus mutans* strain 6715 was used. First, 200 μl of 150 μM dextran T-10 (produced by Pharmacia Aktiebolag) was mixed with 100 μl of 100 U GTase. Then, 20 μl of 500 mM phosphate buffer (pH 6.5) and 500 μl of test saccharide solution were added to the mixture so as to be thoroughly mixed to give a solution in a total amount of 1 ml. The solution was allowed to react at 37° C. for 15 hours and centrifuged to collect a precipitate. The collected precipitate was washed with distilled water a couple of times and suspended in 500 μl of distilled water. The concentration of saccharide in the suspension thus obtained was measured by the phenol-sulfuric acid method. As the test saccharide solution, the phosphorylated saccharide of Example 1 was used and prepared at the final concentration of 10%, 5%, 1%, and 0% in the reaction solutions. On the other hand, the same test was conducted, using 5% sucrose as a control. Table 3 shows the results.

TABLE 3

| saccharide | Concentration (%) | Concentration of saccharide (%) in precipitate |
|---|---|---|
| Phosphorylated saccharide | 10 | ND |
|  | 5 | ND |
|  | 1 | ND |
|  | 0 | ND |
| Sucrose | 5 | 0.317 |

It was found in the present example that the phosphorylated saccharide itself did not become a substrate for GTase and did not generate glucan.

Example 22

When four percent soluble starch aqueous solution which is fully gelatinized by heating is kept at 4° C., the soluble starch rapidly retrogrades and the starch aqueous solution becomes turbid. The effect of the phosphorylated saccharide of suppressing the retrogradation of starch was examined as follows.

Figure 26:
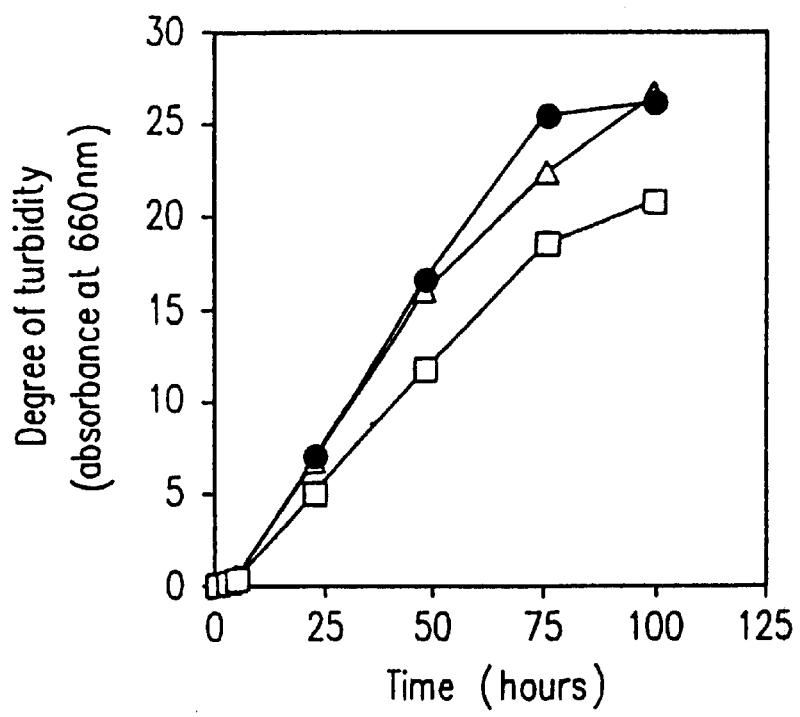
FIG. 26 is a graph showing the effect of suppressing the retrogradation of starch of the phosphorylated saccharide of Example 1 of the present invention.

Soluble starch was dissolved in distilled water at the final concentration of 4%. Then, 4% phosphorylated saccharide of Example 1 (represented by □ in the figure) was added to the solution thus obtained. The resulting solution was kept at 4° C. and its turbidity was measured at 660 nm with the passage of time, whereby the degree of generation of a precipitate caused by retrogradation was examined. For comparison, Fujioligo #360 produced by Nihon Shokuhin Kako Co., Ltd. (60% or more maltotriose) (represented by Δ in the figure), which is considered to have an effect of suppressing the retrogradation of starch, was used. As a blank, distilled water (represented by ● in the figure) was used. FIG. 26 shows the results. In this figure, the horizontal axis represents a reaction time (hours), and the vertical axis represents a degree of turbidity (absorbance at 600 nm).

It was found in the present example that the degree of turbidity when using the phosphorylated saccharide was smaller than the case of using Fujioligo. Thus, the phosphorylated saccharide was confirmed to have an effect of suppressing the retrogradation of starch.

Example 23

Figure 27:
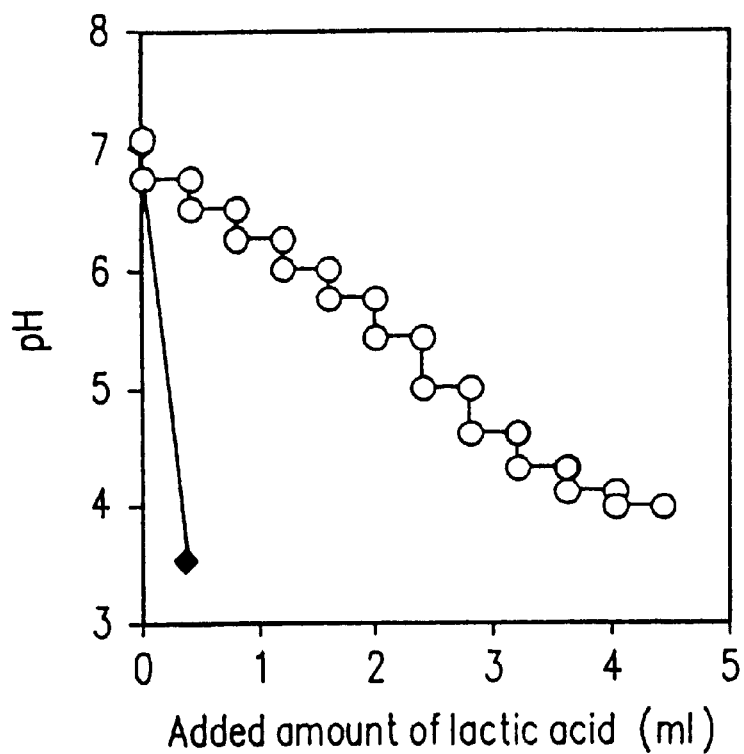
FIG. 27 is a graph showing the buffer function of the phosphorylated saccharide of Example 1 of the present invention.

The buffer function of phosphorylated saccharide was examined as follows. First, 0.1 N lactic acid was dropped at a rate of 0.4 ml per minute to 30 ml of 1% phosphorylated saccharide solution of Example 1 (represented by ○ in the figure), and the decrease in pH was measured with the passage of time. Lactic acid was dropped to 30 ml of distilled water as a control (represented by ◆ in the figure). FIG. 27 shows the results. In this figure, the horizontal axis represents the amount of added lactic acid (ml), and the vertical axis represents the change in pH.

In the present example, it was found that the pH in control was decreased to 3.5 by the addition of 0.4 ml of lactic acid, while the phosphorylated saccharide has a buffer function for preventing the rapid change in pH.

Example 24

The balance test of calcium using a rat was conducted as follows.

Four-week-old Sprague-Dawley rats were obtained from Nippon CLEA and bred in separate cages in an atmosphere of a temperature of 23.1±1.0° C., a humidity of 55±7%, and light and dark cycles once every 12 hours. The rats were pre-bred on AIN-76 refined feed for the first one week, and they were divided into three groups each having 6 rats so that each group included the rats with the same weight. Then, one group was fed on the phosphorylated saccharide of Example 1; another group was fed on the phosphorylated saccharide of Example 4; and the other group was fed on diet without the phosphorylated saccharide as a control, respectively for 5 weeks. The composition of each diet is shown in Table 4.

TABLE 4

| | Composition of diet (g/100 g diet) | | |
|---|---|---|---|
| | Group 1 | Group 2 | Group 3 |
| ISP | 20.0 | 20.0 | 20.0 |
| Corn starch | 66.9 | 63.4 | 63.4 |
| Corn oil | 5.0 | 5.0 | 5.0 |
| Cellulose powder | 0.5 | 0.5 | 0.5 |
| Vitamin mix. | 0.8 | 0.8 | 0.8 |
| Choline chloride | 0.2 | 0.2 | 0.2 |
| Mineral mix.** | 4.0 | 4.0 | 4.0 |
| $CaCO_3$ | 0.4 | 0.4 | 0.4 |
| $CaHPO_4$ | 0.6 | 0.6 | 0.6 |
| $KH_2PO_4$ | 1.6 | 1.6 | 1.6 |
| PO*** | — | — | 3.5 |
| MS**** | — | 3.5 | — |

*ISP: Isolated soybean protein
**Mineral mix.: Ca and P free
***PO: Phosphorylated saccharide of Example 1
****MS: Phosphorylated saccharide of Example 4
Final concentration of Ca; 0.35%, Pi; 0.7%

Figure 28:
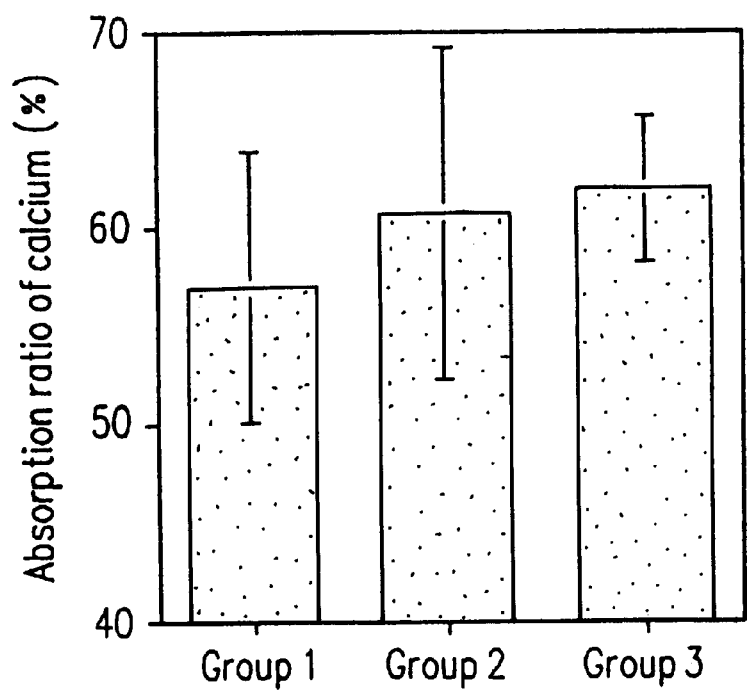
FIG. 28 is a graph showing the calcium absorption ratio of rats fed with the phosphorylated saccharide of the present invention.
Figure 29:
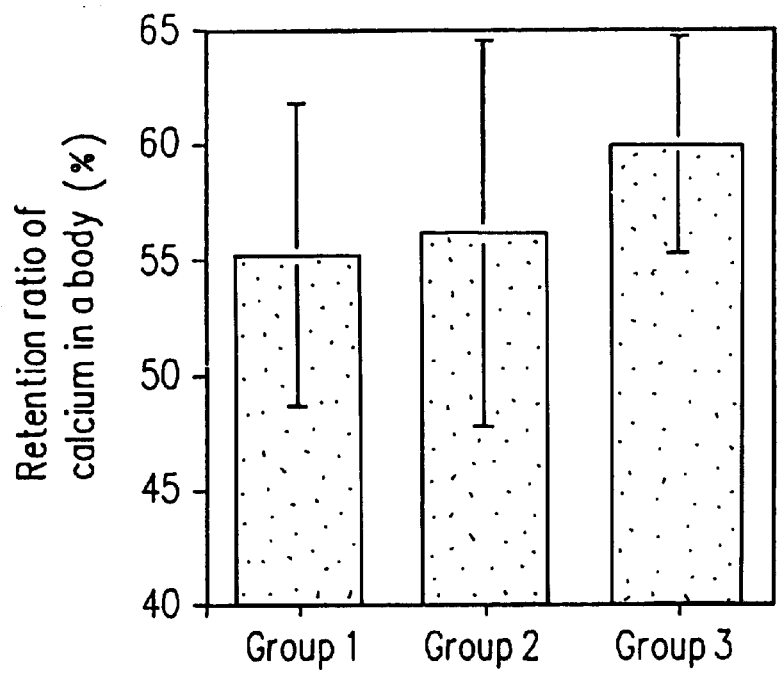
FIG. 29 is a graph showing the calcium retention ratio in a body of rats fed with the phosphorylated saccharide of the present invention.

Each rat was weighted once a week, and the intake of the diet was measured once every 2 to 3 days. The balance of calcium was measured and urine and feces were collected three days before the completion of the experiment. There was no difference in the increase in weight between the groups; each rat weighed about 360 g. FIG. 28 shows the absorption ratio obtained from the balance test of calcium. In this figure, the horizontal axis represents the group of rats, and the vertical axis represents the absorption ratio of calcium. FIG. 29 shows the retention ratio (%) of calcium in a body. In this figure, the horizontal axis represents the group of rats, and the vertical axis represents the retention ratio (%) of calcium in a body.

In FIG. 28, the absorption ratio of calcium obtained from the balance test was calculated as follows: The dry weight of the collected feces was measured. Then, a predetermined amount thereof was incinerated and extracted with 1 N hydrochloric acid. The extract solution was subjected to atomic absorption spectroscopy to determine the amount of calcium. The amount of calcium thus obtained was substituted into the following formula to calculate the absorption ratio.

Absorption ratio of calcium=[(Intake of Ca−Amount of Ca discharged into feces)]/Intake of Ca]×100

In FIG. 29, the calcium retention ratio in a body was calculated as follows: The dry weight of the collected feces was measured. Then, a predetermined amount thereof was incinerated and extracted with 1 N hydrochloric acid. The extract solution and the urine were subjected to atomic absorption spectroscopy to obtain the amount of calcium therein. The amount of calcium was substituted into the following formula to calculate the retention ratio of calcium in a body.

Retention ratio of calcium in a body=[(Intake of Ca−Amount of Ca discharged into feces−Amount of Ca discharged into urine)/Intake of Ca]×100

In the present example, it was found that the absorption ratio of calcium is likely to increase by the administration of the phosphorylated saccharide, and the effect of promoting the absorption of calcium was observed. Furthermore, it was found that the retention ratio of calcium in a body is likely to improve.

Example 24

Figure 30:
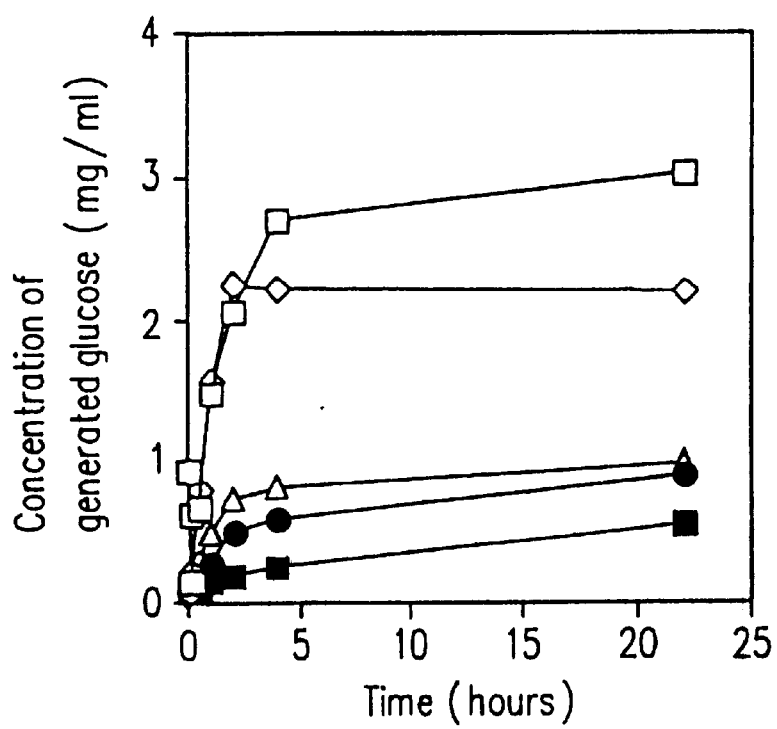
FIG. 30 is a graph showing the results of the digestive test of the phosphorylated saccharide of the present invention.

A digestion test of phosphorylated saccharide was conducted by a simplified method for evaluating saccharide digestion of Hirayama et al. (Denpun Kagaku, vol. 37, No. 4, pp. 259–262, 1990). More specifically, distilled water was added to acetone powder of the small intestine of rats (produced by Sigma Chemical Company) to give 100 mg/ml of suspension. The suspension was applied to an ultrasonicator (SONIFIER cell disrupter: 1% duty cycle 50, 1 min.×3 times) and centrifuged. Thereafter, the supernatant was obtained as an enzyme solution. Then, 50 μl each of the enzyme solution was mixed with 50 μl of test saccharide solution, and the mixture was allowed to react at 37° C. for 0 min., 5 min., 10 min., 30 min., 1 hour, 2 hours, 4 hours, and 22 hours, respectively. These reaction solutions were placed in a boiling water bath for 5 minutes to terminate the reaction. Then, the amount of glucose generated in accordance with a glucose oxidase method (A. Dahlqvist, Anal. Biochem., vol. 7, pp. 18–25, 1964) was measured, and its digestive property was examined. As the test saccharide solution, 0.5% phosphorylated saccharide of Example 1 (represented by ● in the figure), PO-2 fraction of Example 2 (represented by ■ in the figure), glucose-6-phosphate (represented by Δ in the figure), palatinose (represented by ◇ in the figure), and maltotriose (represented by □ in the figure) were used. FIG. 30 shows the results. In this figure, the horizontal axis represents a treatment time (hours), and the vertical axis represents the concentration of generated glucose (mg/ml).

It was found in the present example that the phosphorylated saccharide is less digestive than palatinose and maltotriose.

Example 25

The phosphorylated saccharide of Example 1 was examined for the keeping quality of carnations. Six cut carnations (coral var.) were respectively placed in 300 ml of the following aqueous solutions at 20° C. under the light and dark cycle once every 12 hours. Then, the number of healthy flowers after a certain period of time was examined. Table 5 shows the composition of the aqueous solutions used in the present example. As water, deionized water was used.

TABLE 5

| No. | Composition of solution |
|---|---|
| 1 | 0.2% phosphorylated saccharide (Example 1) solution |
| 2 | 1.5 mM calcium chloride solution |
| 3 | 0.2% phosphorylated saccharide + 1.5 mM calcium chloride solution |

The examination was conducted on the 4th, 7th, and 14th day from the day when those flowers were placed in the aqueous solutions. On the 4th, 7th, and 14th day, each aqueous solution was replaced by a new one. Table 6 shows the results.

TABLE 6

| | Number of healthy flowers | | | Amount of water |
|---|---|---|---|---|
| No. | 4th day | 7th day | 14th day | absorbed by flowers (ml) |
| 1 | 3 | 1 | 1 | 245 |
| 2 | 5 | 3 | 2 | 235 |
| 3 | 5 | 5 | 5 | 280 |

Figure 31:
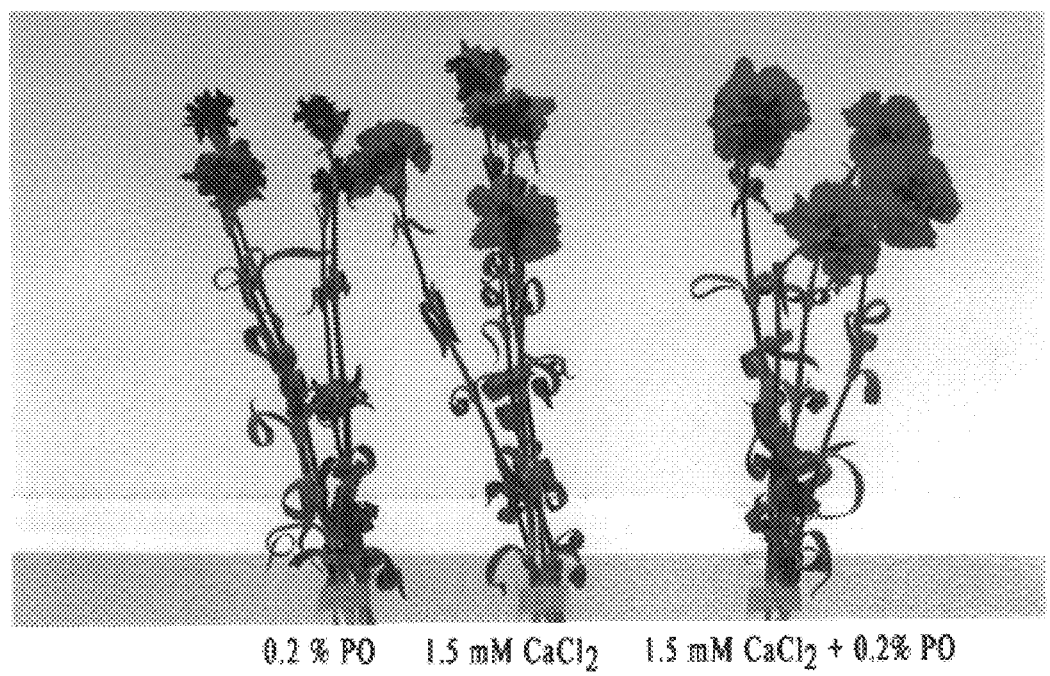
FIG. 31 is a biological morphological picture showing the state of cut flowers treated with the phosphorylated saccharide of the present invention.

In the presence of the phosphorylated saccharide and calcium, the cut flower was almost healthy on the 14th day; thus, the keeping quality effect of the phosphorylated saccharide was confirmed. FIG. 31 shows the state of the cut flowers on the 7th day. The most healthy flower and the most unhealthy flower were excluded from this picture.

Example 26

The phosphorylated saccharide of Example 1 was examined for the effect on the growth of a radish sprout. Twenty seeds of the radish sprout were respectively placed on Petri dishes having absorbent cotton with 30 ml of the following aqueous solution added, and each seedling was obtained by cutting off root portion from the absorbent cotton after 9 days. The growth state of the seedling was observed. As a fertilizer containing phosphorus, 1000-fold diluted solution of Hyponex (produced by Hyponex Co., Ltd.) was used. The Petri dishes were placed in a transparent sealed container so that solutions were not dried. Table 7 shows the composition of the aqueous solution used in the present example. As water, deionized water was used.

TABLE 7

| No. | Composition of Solution |
|---|---|
| 1 | Water |
| 2 | 15 mM calcium chloride solution |
| 3 | Hyponex solution |
| 4 | 15 mM calcium chloride + Hyponex solution |
| 5 | Hyponex solution + 1% phosphorylated saccharide solution |
| 6 | 15 mM calcium chloride + Hyponex solution + 1% phosphorylated saccharide solution |

The seedlings thus obtained were measured for elongation and weight thereof. Table 8 shows the measurement results.

TABLE 8

| No. | Average elongation (cm) | Average weight (g) |
|---|---|---|
| 1 | 5.72 | 0.13 |
| 2 | 5.87 | 0.17 |
| 3 | 7.98 | 0.17 |
| 4 | 8.18 | 0.18 |
| 5 | 7.11 | 0.16 |
| 6 | 9.09 | 0.21 |

As shown in Table 8, when using the combination of Hyponex, calcium, and phosphorylated saccharide, the most satisfactory elongation was observed. Thus, the effect of the phosphorylated saccharide was confirmed.

Example 27

Attempts to chemically phosphorylate various saccharides were made. Polysaccharides composed of glucose or constituent saccharides other than glucose, such as xanthan gum, tamarind gum, guar gum, Locust bean gum, gellan gum, fucoidan, agar, dextran, and mannan; or cyclic oligosaccharides such as α-cyclodextrin were attempted to be phosphorylated by a method for producing phosphorylated starch described in Denpun Kagaku Handbook (ed. J. Nikuni, Asakura Shoten, pp. 510–511, 1977). After the reaction, those phosphorylated saccharides were dissolved in about 40 ml of deionized water. Insoluble substance in each solution were removed by centrifugation (at 8,000 rpm, for 20 min.), and the resultant solution was dialyzed to completely remove the salts therein. Then, the solution was lyophilized. Each powdery sample was examined for the calcium solubilization effect by the method described in Example 12. The final concentration of each sample was made to 0.5%. Table 9 shows the results. This table shows the soluble calcium ratio to calcium added 2 hours after the shaking.

TABLE 9

Soluble calcium ratio 2 hours after shaking in each saccharide

| saccharide | Soluble Ca (%) |
| --- | --- |
| xanthan gum | 61.4 |
| tamarind gum | 100.0 |
| guar gum | 80.9 |
| Locust bean gum | 58.2 |
| gellan gum | 29.2 |
| fucoidan | 53.7 |
| α-cyclodextrin | 24.1 |
| agar | 49.3 |
| dextran | 27.7 |
| mannan | 90.7 |

The calcium solubilization effect was not recognized in the untreated saccharides; however, it was confirmed in the treated saccharides.

The phosphorylated saccharide of the present invention is suitable for foods taken by growing infants and pregnant women requiring calcium, magnesium and ion, and people during illness or those after illness, as well as mixed feeds for animals and fertilizers for plants. Furthermore, the phosphorylated saccharide exhibits the effect of promoting the absorption of alkaline earth metals such as calcium and magnesium, and iron, even when being used directly, i.e., without being diluted, for fertilizers, feeds, or foods. The phosphorylated saccharide is not harmful to a living body, because it is derived from natural substances. The phosphorylated saccharide of the present invention is hard to digest and is low in calories. Thus, the phosphorylated saccharide can be expected to have the effect of growing *Bifidobacterium bifidum* and the function of preventing the intestinal disorders, as reported with respect to many oligosaccharides. In addition, the phosphorylated saccharide of the present invention is preferred as detergents safe with respect to a living body and as dentalis lapis preventives.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for producing a phosphorylated saccharide in the form of a glucan or cyclodextrin having at least one phosphate group per molecule, comprising the step of allowing an enzyme selected from the group consisting of starch degrading enzyme, glycosyltransferase, and a combination of starch degrading enzyme and glycosyltransferase to act on starch having a phosphate group or chemically modified starch, wherein the starch degrading enzyme includes a combination of (i) an endo-type starch degrading enzyme selected from the group consisting of α-amylase and neopullulanase, (ii) an exo-type starch degrading enzyme selected from the group consisting of β-amylase and glucoamylase, and (iii) a debranching enzyme selected from the group consisting of isoamylase and pullulanase.

2. A method for producing a phosphorylated saccharide according to claim 1, wherein the saccharide is glucan and the enzyme is starch degrading enzyme.

3. A method for producing a phosphorylated saccharide according to claim 1, wherein the saccharide is glucan and the enzyme is glycosyltransferase.

4. A method for producing a phosphorylated saccharide according to claim 3, wherein the glycosyltransferase is cyclodextrin glucanotransferase.

5. A method for producing a phosphorylated saccharide comprising the step of allowing glycosyltransferase to act on a phosphorylated saccharide in the form of a glucan or cyclodextrin having at least one phosphate group per molecule.

6. A method for producing a phosphorylated saccharide according to claim 5, wherein the glycosyltransferase is cyclodextrin glucanotransferase.

* * * * *

UNITED STATES PATENT AND TRADEMARK OFFICE
CERTIFICATE OF CORRECTION

PATENT NO.   : 6,268,182 B1  
DATED        : July 31, 2001  
INVENTOR(S)  : Hiroshi Kamasaka, Shigetaka Okada, Kaname Kusaka, Kazuya Yamamoto and Kenji Yoshikawa It is certified that error appears in the above-identified patent and that said Letters Patent is hereby corrected as shown below:

<u>Title page,</u>
Item [54], in the title change "METHOD AND PRODUCING PHOSPHORYLATED SACCHARIDES" to -- METHOD FOR PRODUCING PHOSPHORYLATED SACCHARIDES --.

Signed and Sealed this

Eighteenth Day of June, 2002

*Attest:*

JAMES E. ROGAN  
*Director of the United States Patent and Trademark Office*

*Attesting Officer*